US010643742B2

(12) United States Patent
Hogg et al.

(10) Patent No.: US 10,643,742 B2
(45) Date of Patent: *May 5, 2020

(54) REAL TIME ADAPTIVE CONTROLLER MEDICATION DOSING

(71) Applicant: Reciprocal Labs Corporation, Madison, WI (US)

(72) Inventors: Christopher Hogg, San Francisco, CA (US); Gregory F. Tracy, Madison, WI (US); John David Van Sickle, Oregon, WI (US); Dmitry Stupakov, Cupertino, CA (US); Ki Hong Han, Dublin, CA (US); Mike Lohmeier, Sun Prairie, WI (US); John Kalmi, Wauwatosa, WI (US); Leah Morrell, Madison, WI (US); Charles Clayton Donaldson, Madison, WI (US)

(73) Assignee: Reciprocal Labs Corporation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/292,303

(22) Filed: Mar. 4, 2019

(65) Prior Publication Data

US 2019/0272910 A1    Sep. 5, 2019

Related U.S. Application Data

(63) Continuation of application No. 15/351,197, filed on Nov. 14, 2016, now Pat. No. 10,255,412.

(Continued)

(51) Int. Cl.
*G16H 20/13*    (2018.01)
*G06F 19/00*    (2018.01)
(Continued)

(52) U.S. Cl.
CPC ........ *G16H 20/13* (2018.01); *A61M 15/0001* (2014.02); *A61M 15/009* (2013.01);
(Continued)

(58) Field of Classification Search
CPC ... G16H 20/01; G16H 20/13; A61M 15/0001; A61M 15/009; A61M 2202/064;
(Continued)

(56) References Cited

U.S. PATENT DOCUMENTS

| 5,284,133 A | 2/1994 | Burns et al. |
| 5,363,842 A | 11/1994 | Mishelevich et al. |

(Continued)

OTHER PUBLICATIONS

Bateman, E.D., et al. "Can Guideline-Defined Asthma Control be Achieved? The Gaining Optimal Asthma Control Study," Am. J. Respir. Crit. Care Med. Oct. 15, 2004, pp. 836-844, vol. 170, No. 8.

(Continued)

*Primary Examiner* — Mohamed Barakat
(74) *Attorney, Agent, or Firm* — Fenwick & West LLP

(57) ABSTRACT

Systems and methods for monitoring accurate, real-time medicament device events, performing analytics on that data, and providing notifications are described. In various embodiments, an application server receives controller medication events, analyzes the events, associated event times, and controller medication dosage plans to characterize event times and send notifications for future doses. The controller medication dosage plan may specify a dose time for a planned dose, a narrow time window comprising the dose time, and an expanded time window comprising the narrow time window and longer in duration than the narrow time window, and the events may be characterized based on their time relative to the dose time, the time windows, and other events.

16 Claims, 25 Drawing Sheets

Related U.S. Application Data

(60) Provisional application No. 62/255,213, filed on Nov. 13, 2015.

(51) Int. Cl.
*A61M 15/00* (2006.01)
*G08B 21/24* (2006.01)
*G08B 25/08* (2006.01)
*H04W 76/14* (2018.01)
*H04W 4/80* (2018.01)

(52) U.S. Cl.
CPC ......... *G06F 19/3462* (2013.01); *G08B 21/24* (2013.01); *G08B 25/08* (2013.01); *A61M 2202/064* (2013.01); *A61M 2205/18* (2013.01); *A61M 2205/3368* (2013.01); *A61M 2205/3553* (2013.01); *A61M 2205/3584* (2013.01); *A61M 2205/50* (2013.01); *A61M 2205/505* (2013.01); *A61M 2205/52* (2013.01); *A61M 2205/581* (2013.01); *H04W 4/80* (2018.02); *H04W 76/14* (2018.02)

(58) Field of Classification Search
CPC ...... A61M 2205/18; A61M 2205/3368; A61M 2205/3553; A61M 2205/3584; A61M 2205/50; A61M 2205/505; A61M 2205/52; A61M 2205/581; G08B 21/24; G08B 25/08; H04W 76/14; H04W 4/80; G06F 19/3462
See application file for complete search history.

(56) References Cited

U.S. PATENT DOCUMENTS

| | | | |
|---|---|---|---|
| 5,477,849 A | 12/1995 | Fry | |
| 5,505,192 A | 4/1996 | Samiotes et al. | |
| 5,544,647 A | 8/1996 | Jewett et al. | |
| 5,622,163 A | 4/1997 | Jewett et al. | |
| 5,809,997 A | 9/1998 | Wolf | |
| 5,976,082 A | 11/1999 | Wong et al. | |
| 6,076,521 A | 6/2000 | Lindahl et al. | |
| 6,190,326 B1 | 2/2001 | McKinnon et al. | |
| 6,202,642 B1 | 3/2001 | McKinnon et al. | |
| 6,540,672 B1 | 4/2003 | Simonsen et al. | |
| 6,579,231 B1 | 6/2003 | Phipps | |
| 6,637,430 B1 | 10/2003 | Voges et al. | |
| 6,652,455 B1 | 11/2003 | Kocher | |
| 6,729,327 B2 | 5/2004 | McFarland | |
| 6,743,202 B2 | 6/2004 | Hirschman et al. | |
| 6,747,556 B2 | 6/2004 | Medema et al. | |
| 6,804,558 B2 | 10/2004 | Haller et al. | |
| 6,937,150 B2 | 8/2005 | Medema et al. | |
| 6,958,691 B1 | 10/2005 | Anderson et al. | |
| 7,151,456 B2 | 12/2006 | Godfrey | |
| 7,191,777 B2 | 3/2007 | Brand et al. | |
| 7,481,213 B2 | 1/2009 | Childers | |
| 7,537,005 B2 | 5/2009 | Dave | |
| 7,766,012 B2 | 8/2010 | Scheuch et al. | |
| 9,550,031 B2 | 1/2017 | Van Sickle et al. | |
| 9,997,039 B1* | 6/2018 | Heaton | G08B 21/0423 |
| 2002/0073196 A1 | 6/2002 | Westervelt et al. | |
| 2003/0098022 A1 | 5/2003 | Nakao et al. | |
| 2003/0221687 A1 | 12/2003 | Kaigler | |
| 2004/0148199 A1 | 7/2004 | Dixon | |
| 2004/0199056 A1 | 10/2004 | Husemann et al. | |
| 2005/0021286 A1 | 1/2005 | Kunce | |
| 2005/0028815 A1 | 2/2005 | Deaton et al. | |
| 2005/0086256 A1 | 4/2005 | Owens | |
| 2005/0150488 A1 | 7/2005 | Dave | |
| 2005/0172958 A1 | 8/2005 | Singer et al. | |
| 2005/0247312 A1 | 11/2005 | Davies | |
| 2006/0089545 A1 | 4/2006 | Ratjen et al. | |
| 2006/0231109 A1 | 10/2006 | Howell et al. | |
| 2006/0237001 A1 | 10/2006 | Stangl | |
| 2006/0237002 A1 | 10/2006 | Bonney et al. | |
| 2007/0023034 A1 | 2/2007 | Jongejan et al. | |
| 2007/0186923 A1 | 8/2007 | Poutiatine et al. | |
| 2007/0271298 A1 | 11/2007 | Jung et al. | |
| 2008/0125724 A1 | 5/2008 | Monroe | |
| 2008/0201169 A1 | 8/2008 | Galasso et al. | |
| 2008/0255874 A1 | 10/2008 | Crooks et al. | |
| 2008/0281636 A1 | 11/2008 | Jung et al. | |
| 2009/0128330 A1 | 5/2009 | Monroe | |
| 2009/0281835 A1 | 11/2009 | Patwardhan et al. | |
| 2009/0326861 A1* | 12/2009 | Langford | A61M 15/009 702/173 |
| 2010/0192948 A1 | 8/2010 | Sutherland et al. | |
| 2010/0252036 A1 | 10/2010 | Sutherland et al. | |
| 2011/0253139 A1 | 10/2011 | Guthrie et al. | |
| 2011/0290256 A1 | 12/2011 | Sather et al. | |
| 2012/0209241 A1 | 8/2012 | Drew et al. | |
| 2013/0184682 A1 | 7/2013 | Austin et al. | |
| 2014/0244033 A1 | 8/2014 | Ucer et al. | |
| 2015/0061867 A1* | 3/2015 | Engelhard | G06Q 50/22 340/539.18 |
| 2016/0012205 A1* | 1/2016 | Saint | A61M 5/31528 604/154 |

OTHER PUBLICATIONS

Frey, U. et al., "Complexity of Chronic Asthma and Chronic Obstructive Pulmonary Disease: Implications for Risk Assessment, and Disease Progression and Control," Lancet, Sep. 20, 2008, pp. 1088-1099, vol. 372.

International Search Report for Application No. PCT/US2010/20055 dated May 25, 2010 (2 pages).

Moorman, J.E. et al., "National Surveillance for Asthma—United States," 1980-2004. Morbidity and Mortality Weekly Report (MMWR), Centers for Disease Control and Prevention, Oct. 19, 2007, 14 pages, 56, No. SS-8.

Nathan, R.A., et al. "Development of the Asthma Control Test: a Survey for Assessing Asthma Control," J. Allergy Clin. Immunol., Jan. 2004, pp. 59-65, vol. 113, No. 1.

National Heart, Lung, and Blood Institute. Expert Panel Report 3: Guidelines for the Diagnosis and Management of Asthma Full Report 2007, National Asthma Education and Prevention Program, U.S. Department of Health and Human Services, National Institutes of Health, 2007, 440 pages.

PCT International Search Report and Written Opinion, PCT Application No. PCT/US14/39014, dated Oct. 23, 2014, 16 pages.

United States Office Action, U.S. Appl. No. 15/351,197, dated Jul. 6, 2018, 8 pages.

* cited by examiner

310o — Time of Day Trend
100% of your events occur during the Afternoon.

310p — Symptom Trend
You reported that 67% of your events display the symptom Chest Tightness.

310q — Day of Week Trend
100% of your events occur on Monday.

310r — Trigger Trend
You reported that 33% of your events were triggered by Smells or Scents.

310u

Quick Survey

In the past 4 weeks, how often has hour asthma kept you from getting things done at work, school, or home?

| All of the time |
|---|

| Most of the time |
|---|

| Some of the time |
|---|

| A little of the time |
|---|

| None of the time |
|---|

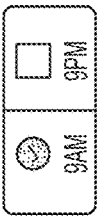
FIG. 5C
FIG. 5D
FIG. 5E
FIG. 5F
FIG. 5G

REAL TIME ADAPTIVE CONTROLLER MEDICATION DOSING

CROSS-REFERENCE TO RELATED APPLICATION

This application is a continuation of U.S. patent application Ser. No. 15/351,197 filed on Nov. 14, 2016, which claims the benefit of U.S. Provisional Application No. 62/255,213, filed Nov. 13, 2015, both of which are incorporated by reference herein in their entirety for all purposes.

BACKGROUND

Field of Art

The disclosure relates generally to medicament device usage, and more specifically to device usage, analyzing adherence with respect to medicament treatment plans, and providing information to patients and other parties based on that analysis.

Description of the Related Art

Asthma remains a significant and costly public health problem. In the United States, more than 22 million people have the disease. Worldwide, the World Health Organization estimates the population with asthma may be 300 million, and predicts that it will rise to 400 million by 2025.

Despite the development of new medications, rates of hospitalizations and emergency room visits have not declined. Each year in the United States the disease causes approximately 2 million emergency department visits, 500,000 hospitalizations, and 5,000 deaths. In addition, asthma is responsible for an estimated 15 million missed days of school, and 12 million days of work. Total annual costs to US health insurers and employers are greater than $18 billion.

The majority of these exacerbations could be prevented with currently available treatments, however, only 1 in 5 asthmatics has the disease under control. Newly revised national guidelines urge doctors to more closely monitor whether treatment is controlling everyday symptoms and improving quality of life. Physicians, however, have few available tools to assess how well their patients are doing day-to-day. An increasing number of physicians have begun to use periodic, written questionnaires (such as the Asthma Control Test) to monitor patients and determine their level of control. These instruments require patients to accurately recall and report the frequency of symptoms, inhaler usage, and activity level and restriction over some period of time (usually two to four weeks). As a result, these questionnaires are subject to error introduced by biases (recall), different interpretations of symptoms, and behaviors (non-adherence), and only provide information at the time they are used.

SUMMARY

An adherence analytics system is a unified platform for monitoring accurate, real-time medicament device usage, performing analytics on that data, and providing notifications according to the analytics. The adherence analytics system receives respiratory medication events by receiving notifications from a sensor attached to a medicament device (e.g. inhaler) used by a patient who has authorized the analytics system to help manage their respiratory disease (e.g., asthma, COPD, etc.). The sensor, when attached to or incorporated in a metered dose inhaler or other medicament device, records the geographical location, time, and date where and when a rescue or controller medication event takes place, and communicates that information to the analytics system. The analytics system analyzes the received events (both the most recent and previously received events) in real time or near-real time, and delivers timely information on the use of inhaled medications to inform and guide management of the disease, including alerts to patients and the healthcare providers and information regarding a patient's adherence to a medication plan. The information may include instructions to take or not take a planned dose, periodic summaries of adherence, and other messages to encourage better adherence behavior. By providing information regarding a patient's adherence to a medication plan, the analytics system can assist patients in better managing respiratory diseases.

BRIEF DESCRIPTION OF DRAWINGS

FIGS. 3B-3N illustrate example cards displayed within the dashboard of the client application, according to one embodiment.

FIG. 5A illustrates a first embodiment for determining whether to recommend that the patient take their next dose, as may be included in a notification sent to the patient's device.

FIG. 5B illustrates an example of the timeline of the first embodiment for a dosing plan that specifies that a dose is to be taken four times a day.

FIGS. 5C-5G illustrate additional examples of timelines of the first embodiment for a dosing plan that specifies that a dose is to be taken twice a day.

DETAILED DESCRIPTION

I. System Environment

Figure 1:
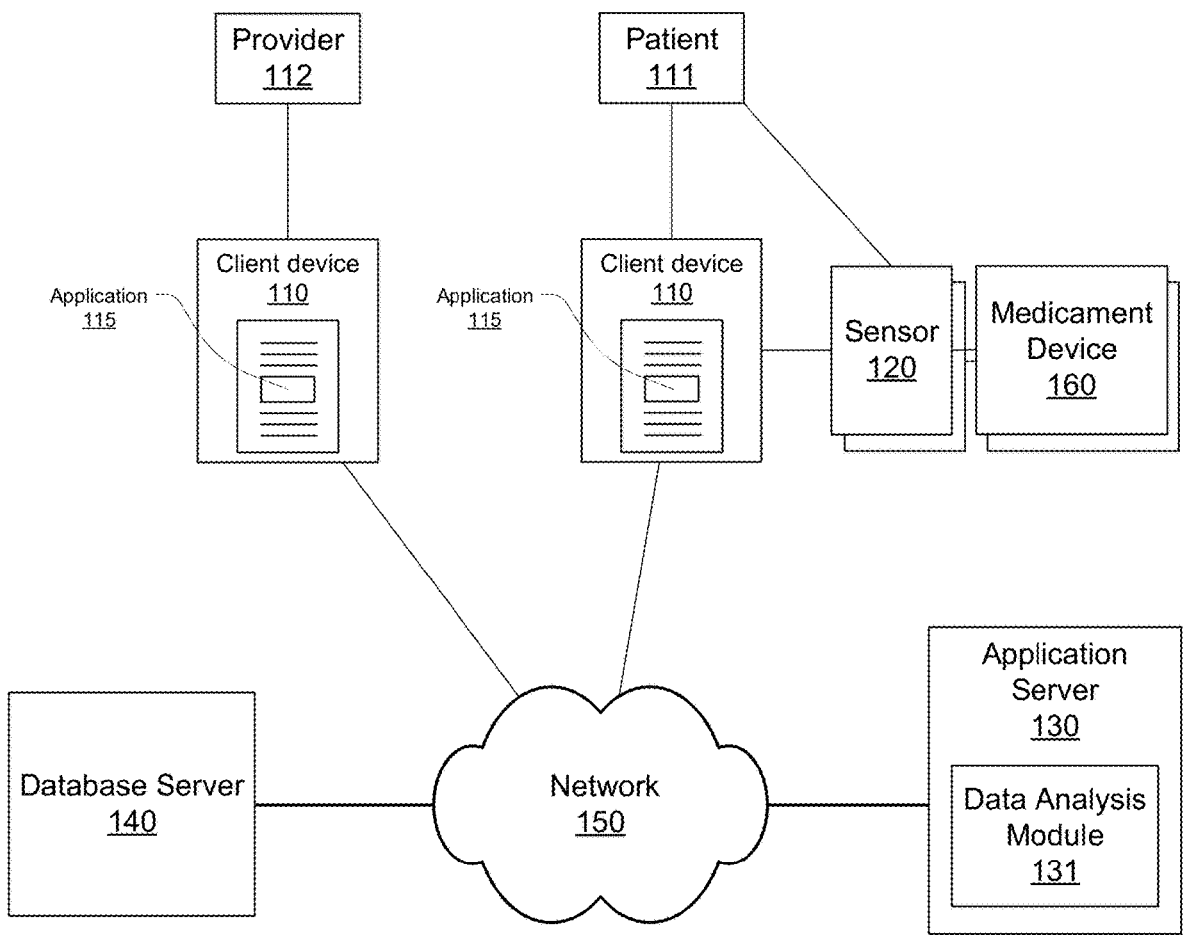
FIG. 1 shows an analytics system for monitoring accurate, real-time medicament device usage, performing analytics on that data, and providing notifications according to the analytics, according to one embodiment.

FIG. 1 shows an analytics system 100 for monitoring accurate, real-time medicament device events, performing analytics on that data, and providing notifications, according to one embodiment.

The analytics system includes client computing devices 110, a medicament device sensor 120, a medicament device 160, an application server 130, database server 140, and a network 150. Although FIG. 1 illustrates only a single instance of most of the components of the analytics system 100, in practice more than one of each component may be present, and additional or fewer components may be used.

I.A. Client Device and Application

The client devices 110, at the behest of their users, interact with the analytics system 100 via the network 150. For purposes of explanation and clarity it is useful to identify at least two different types of users. A patient 111 is a user burdened with respiratory impairment who makes use of the analytics system 100 at least in part to obtain personalized notifications provided by the server 130 and by their health care provider 112. Such notifications can be provided in exchange for the user's permission to allow the analytics system 100 to monitor the patient's 111 medicament device 160 usage. As will be explained below, medication events are detected by a sensor 120 associated with the medicament device 160 and the user's client device 100, which in turn reports to the application server 130, which in turn can initiate a process to generate risk notifications which are provided to the user through the client device 110.

Another type of user is a healthcare provider 112 who, again with the patient's 111 express permission, also receives notifications regarding a patient's management, as well as aggregated rescue or controller medication event data and derived statistics based on these events and other associated data. Other types of users are also contemplated, such as parents/guardians of patients 111 who may also with to receive notifications in the event that their own client devices 110 are distinct from that of their children.

The client device 110 is a computer system, an example physical implementation which is described more completely with respect to FIG. 2, below. The client device 110 is configured to wirelessly communicate with the analytics system 100 via network 150. With network 150 access, the client device 110 transmits to system 100 the user's geographical location and the time of a controller or rescue medication event, as well as information describing the event as received from the associated medicament device sensor 120 (referred to throughout as "sensor 120").

Regarding user location and event times, the client device 110 may determine the geographical location and time of a rescue event through use of information about the cellular or wireless network 150 to which it is connected. For example, the current geographical location of the client device 110 may be determined by directly querying the software stack providing the network 150 connection. Alternatively, the geographical location information may be obtained by pinging an external web service (not shown in FIG. 1) made accessible via network 150. The time of an event can be provided by the sensor 120 as part of the event data or added to event data by querying an appropriate software routine available as part of the client device's native operating system.

In addition to communicating with the application server 130, client devices 110 connected wirelessly to the analytics system 100 may also exchange information with other connected client devices 110. For example, through a client software application 115, a healthcare provider 112 may receive a risk exacerbation notification describing a recent rescue event about a patient 111, then in response send a recommendation to the patient 111 for post-chronic obstructive pulmonary disease (COPD) exacerbation treatment. Similarly, through application 115 patients 111 may communicate with their health care providers 112 other patients 111.

Application 115 provides a user interface (herein referred to as a "dashboard") that is displayed on a screen of the client device 110 and allows a user to input commands to control the operation of the application 115. The dashboard is the mechanism by which healthcare providers 112 and patients 111 access the analytics system 100. For example, the dashboard allows patients 111 and providers 112 to interact with each other, receive notifications, exchange messages about treatment, provide and receive additional event and non-event data, and so on. Application 115 may be coded as a web page, series of web pages, or content otherwise coded to render within an internet browser. Application 115 may also be coded as a proprietary application configured to operate on the native operating system of the client device 110. The dashboard is more completely described below in conjunction with FIG. 3.

In addition to providing the dashboard, application 115 may also perform some data processing on rescue and controller medication event data locally using the resources of client device 110 before sending the processed data through the network 150. Event data sent through the network 110 is received by the application server 130 where it is analyzed and processed for storage and retrieval in conjunction with database server 140. The application server 130 may direct retrieval and storage request to the database system 130 as required by the client application 115.

The client device 110 communicates with the sensor 120 using a network adapter and either a wired or wireless communication protocol, an example of which is the BLUETOOTH Low Energy (BTLE) protocol. BTLE is a short-ranged, low-powered, protocol standard that transmits data wirelessly over radio links in short range wireless networks. After the sensor 120 and client device 110 have been paired with each other using a BTLE passkey, the sensor 120 automatically synchronizes and communicate information relating to medicament device usage with the client device 110. If the sensor 120 hasn't been paired with a client device 110 prior to a rescue medication event, the information is stored locally until such a pairing occurs. Upon pairing, the sensor 120 communicates any stored event records to the client device 110. In other implementations, other types of wireless connections, e.g., infrared or 802.11.

Although client devices 110 and medicament devices 160 are described above as being separate physical devices (such as smart phones and inhalers, respectively), in the future it is contemplated the medicament devices 160 may include not only sensors 120 integrated into a single housing with the device 160, but also aspects of the client device 110. For example, a medicament device 160 may include an audiovisual interface including a display or other lighting elements as well as speakers for presenting visual audible information. In such an implementation the medicament device 160 itself may present the contents of notifications provided by the server 130 directly, in place of or in addition to presenting them through the client devices 110.

I.B. Medicament Device and Sensor

The medicament device 160 is a medical device used to deliver medication to the lungs of a user experiencing constricted respiratory airflow. Medicament devices. (e.g. inhalers) are typically portable and small enough to be carried by hand for ease of accessibility when treating respiratory attacks. In one embodiment, medicine is delivered in aerosol form through a medicament device 160 such as a metered dose inhaler. Metered dose inhalers included a pressured propellant canister of aerosol medicine, a metering valve for delivering a regulated medicine dosage amount, and a plastic holder that holds the pressurized canister and also forms a mouthpiece for delivery of the medicine. In another embodiment, medicine is delivered in dry powder form through a medicament device 160 such as a dry powder inhaler. Dry powder inhalers may have Cartesian ovular shaped bodies that house wheel and gear mechanisms enabling a user to index through a strip of dry powder medication. The bodies of dry powder inhalers also include a manifold and a mouthpiece to deliver dry powder to the user. Examples of controller medications that are dispensed by a controller medicament device 160 include beclomethasone, budesonide, and fluticasone as well as combinations of those medications with a long-acting bronchodilator such as salmeterol or formoterol. Examples of rescue medications that are dispensed by a rescue medicament device 160 include albuterol, salbutamol, levalbuterol, metaproterenol, and terbutaline.

Each patient may be associated with more than one medicament device 160. For example, the patient may have a rescue medicament device 160 that dispenses rescue medication, and a controller medicament device 160 that dispenses controller medication. Similarly, each patient may be associated with more than one sensor 120, each chosen to operate with one of the patient's medicament devices 160.

Generally, a sensor 120 is a physical device that monitors the usage of the medicament dispenser 160. The sensor 120 is either removably attachable to the medicament dispenser without impeding the operation of the medication dispenser, or the sensor 120 is an integrated component that is a native part of the medicament dispenser 160 as made available by its manufacturer.

The sensor 120 includes its own network adapter (not shown) that communicates with the client device 110 either through a wired connection, or more typically through a wireless radio frequency connection. In one embodiment, the network adapter is a BLUETOOTH Low Energy (BTLE) wireless transmitter, however in other embodiments other types of wireless communication may be used (e.g., infrared, 802.11).

The sensor 120 may also be configured to communicate more directly with the application server 130. For example, if the network adapter of the sensor 120 is configured to communicate via a wireless standard such as 802.11 or LTE, the adapter may exchange data with a wireless access point such as a wireless router, which may in turn communicate with the application server 130 without necessarily involving the client device 110 in every exchange of data. These two methods of communicating are not mutually exclusive, and the sensor 120 may be configured to communicate with both the client device 110 and the application server 130, for example using redundant transmission to ensure event data arrives at the application server 130 or to provide information directly to the client device 110 while the application server 130 is determining what notification to provide in response to an event.

As introduced above, the sensor 120 captures data about usage of the medicament device 160. Specifically, each sensor 120 captures the time and geographical location of either controller or rescue medication event, that is, usages of either the controller or rescue medicament device 160, respectively, by the patient 111. Each sensor 120 transmits the event data in real-time or as soon as a network connection is achieved, automatically without input from the patient 111 or health care provider 112. The medication event information is sent to the application server 130 for use in analysis, generation of notifications, and aggregate analyses of event data across multiple patients.

To accomplish this goal, there are a number of different ways for the sensor 120 to be constructed, and in part the construction will depend upon the construction of the medicament device itself 160. Generally, all sensors 120 will include an onboard processor, persistent memory, and the network adapter mentioned above that together function to record, store, and report medication event information to the client device 110 and/or server 130. Sensors 120 may also include a clock for recording the time and date of events.

Regarding specific sensor 120 constructions, traditional inhalers, such as mechanical dose counters, are not designed with sensors 120 in mind, and thus the sensor 120 may be constructed accordingly. Some implementations in this manner include mechanical, electrical, or optical sensors to detect movement of the device 160, priming of the device, activation of the device, inhalation by the user, etc. In contrast, modern inhalers, such as deflectable membrane dose counters, include electrical circuitry may report event information as an electrical data signal which a sensor 120 is designed to receive and interpret, for example the medicament device 160 itself may report movement, priming, and activation to the sensor 120.

More information regarding hardware and software components for the sensors 120 and medicament devices 160, as well as the interaction between them to record one or both of controller and rescue medication events can be found in U.S. patent application Ser. No. 12/348,424, filed Jan. 1, 2009, and International Application No. PCT/US2014/039014, filed May 21, 2014, both of which are incorporated by reference herein in their entirety.

I.C. Application Server

The application server 130 is a computer or network of computers. Although a simplified example is illustrated in FIG. 2, typically the application server will be a server class system that uses powerful processors, large memory, and faster network components compared to a typical computing system used, for example, as a client device 110. The server typically has large secondary storage, for example, using a RAID (redundant array of independent disks) array and/or by establishing a relationship with an independent content delivery network (CDN) contracted to store, exchange and transmit data such as the notifications contemplated above. Additionally, the computing system includes an operating system, for example, a UNIX operating system, LINUX operating system, or a WINDOWS operating system. The operating system manages the hardware and software resources of the application server 130 and also provides various services, for example, process management, input/output of data, management of peripheral devices, and so on. The operating system provides various functions for managing files stored on a device, for example, creating a new file, moving or copying files, transferring files to a remote system, and so on.

The application server 130 includes a software architecture for supporting access and use of the analytics system 100 by many different client devices 110 through network 150, and thus at a high level can be generally characterized as a cloud-based system. The application server 130 generally provides a platform for patients 111 and healthcare providers 112 to report data recorded by the sensors associated with their medicament devices 160 including both rescue medication and controller medication events, collaborate on treatment plans, browse and obtain information relating to their condition and geographic location, and make use of a variety of other functions.

Generally, the application server 130 is designed to handle a wide variety of data. The application server 130 includes logical routines that perform a variety of functions including checking the validity of the incoming data, parsing and formatting the data if necessary, passing the processed data to a database server 140 for storage, and confirming that the database server 140 has been updated.

The application server 130 stores and manages data at least in part on a patient by patient basis. Towards this end, the application server 130 creates a patient profile for each user. The patient profile is a set of data that characterizes a patient 111 of the analytics system 100. The patient profile may include identify information about the patient such as age, gender, current rescue medication, current controller medication, notification preferences, a controller medication adherence plan, and a list of non-patient users authorized to access to the patient profile. The profile may further specify a device identifier, such as a unique media access control (MAC) address identifying the one or more client devices 110 or sensors 120 authorized to submit data (such as controller and rescue medication events) for the patient.

The profile may specify which different types of notifications are provided to patients 111 themselves and their personal healthcare providers 112, as well as the frequency with which notifications are provided. The patient may also authorize their healthcare provider be given access to their patient profile and rescue event history. If the healthcare provider is provided access to the patient profile of the patient, the healthcare provider may specify controller adherence or rescue medication plans. Medication plans may include a prescribed number of doses per day for controller medications.

The application server 130 also creates profiles for health care providers 112. A health care provider profile may include identifying information about the health care provider, such as the office location, qualifications and certifications, and so on. The health care provider profile also includes information about their patient population. The provider profile may include access to all of the profiles of that provider's patients, as well as derived data from those profiles such as aggregate demographic information, rescue and controller medication event patterns, and so on. This data may be further subdivided according to any type of data stored in the patient profiles, such as by geographic area (e.g., neighborhood, city) over by time period (e.g., weekly, monthly, yearly).

The application server 130 receives rescue medication event information from the client device 110 or the sensor 120, triggering a variety of routines on the application server 130. For example, a risk analysis may be performed on rescue and controller medication use for multiple patients to identify medication use based on spatial/temporal clusters (or outbreaks) of medication use based on historically significant permutations from individual, geographic, clinical, epidemiologic, demographic, or spatial or temporal baselines or predicted or expected values. Other types of analyses include daily/weekly adherence trends, adherence changes over time, adherence comparisons to other relevant populations (e.g., all patients, patients on a particular rescue medication or controller medication or combination thereof, identification of triggers (spatial, temporal, environmental), rescue use trends over time, and rescue use comparisons to other relevant populations.

Responsive to any analyses performed, the application server 130 prepares and delivers push notifications to send to patients 111, authorized healthcare providers 112, and/or other users provided access to the patient's profile. Notifications can provide details about the timing, location, and affected patient(s) 111 involved in a medication rescue event. Notifications may additionally comprise a distress or emergency signal that requests emergency assistance that are distributed to emergency assistance providers 112.

In addition to providing push notifications, the server 130 may also provide pull notifications, for example at particular time intervals. Additionally, some notifications (regardless of type) may be triggered not in response to a particular event that has occurred to the patient, but in response to one of the underlying factors of an analysis performed by the server 130 changing. For example, if weather conditions indicate that an increase in air pollution is occurring or is imminent, this may trigger the carrying out of COPD risk analyses for all patients located in the particular geographic area where the pollution is occurring.

Notifications are provided through the network 150 to client applications 115 in a data format specifically designed for use with the client applications, and additionally or alternatively may be provided as short message service (SMS) messages, emails, phone calls, or in other data formats communicated using other communication mediums.

I.D. Database Server

The database server 140 stores data patient and provider data related data such as profiles, medication events, patient medical history (e.g., electronic medical records). Patient and provider data is encrypted for security and is at least password protected and otherwise secured to meet all Health Insurance Portability and Accountability Act (HIPAA) requirements. Any analyses that incorporate data from multiple patients (e.g., aggregate rescue medication event data) and are provided to users is de-identified so that personally identifying information is removed to protect patient privacy.

The database server 140 also stores non-patient data used in analyses. This data includes regional data about a number of geographic regions such as public spaces in residential or commercial zones where patients are physically located and may be exposed to pollutants. This data may specifically include or be processed to obtain a patient's proximity to green space (areas including concentrated numbers of trees and plants) and proximity to different types of human organizations such as may be used to infer a patient's socioeconomic status. One example of regional data includes georeferenced weather data, such as temperature, wind patterns, humidity, the air quality index, and so on. Another example is georeferenced pollution data, including particulate counts for various pollutants at an instance of time or measured empirically. The regional data includes information about the current weather conditions for the time and place of the rescue event such as temperature, humidity, air quality index. All of the items of data above may vary over time, and as such the data itself may be indexed by time, for example separate data points may be available by time of day (including by minute or hour), or over longer periods such as by day, week, month, or season.

Although the database server 140 is illustrated in FIG. 1 as being an entity separate from the application server 130 the database server 140 may alternatively be a hardware component that is part of another server such as server 130, such that the database server 140 is implemented as one or more persistent storage devices, with the software application layer for interfacing with the stored data in the database is a part of that other server 130.

The database server 140 stores data according to defined database schemas. Typically, data storage schemas across different data sources vary significantly even when storing the same type of data including cloud application event logs and log metrics, due to implementation differences in the underlying database structure. The database server 140 may also store different types of data such as structured data, unstructured data, or semi-structured data. Data in the database server 140 may be associated with users, groups of users, and/or entities. The database server 140 provides support for database queries in a query language (e.g., SQL for relational databases, JSON NoSQL databases, etc.) for specifying instructions to manage database objects represented by the database server 140, read information from the database server 140, or write to the database server 140.

I.E. Network

The network 150 represents the various wired and wireless communication pathways between the client 110 devices, the sensor 120, the application server 130, and the database server 140. Network 150 uses standard Internet communications technologies and/or protocols. Thus, the network 150 can include links using technologies such as Ethernet, IEEE 802.11, integrated services digital network (ISDN), asynchronous transfer mode (ATM), etc. Similarly, the networking protocols used on the network 150 can include the transmission control protocol/Internet protocol (TCP/IP), the hypertext transport protocol (HTTP), the simple mail transfer protocol (SMTP), the file transfer protocol (FTP), etc. The data exchanged over the network 150 can be represented using technologies and/or formats including the hypertext markup language (HTML), the extensible markup language (XML), etc. In addition, all or some links can be encrypted using conventional encryption technologies such as the secure sockets layer (SSL), Secure HTTP (HTTPS) and/or virtual private networks (VPNs). In another embodiment, the entities can use custom and/or dedicated data communications technologies instead of, or in addition to, the ones described above.

II. Example Computing Devices

Figure 2:
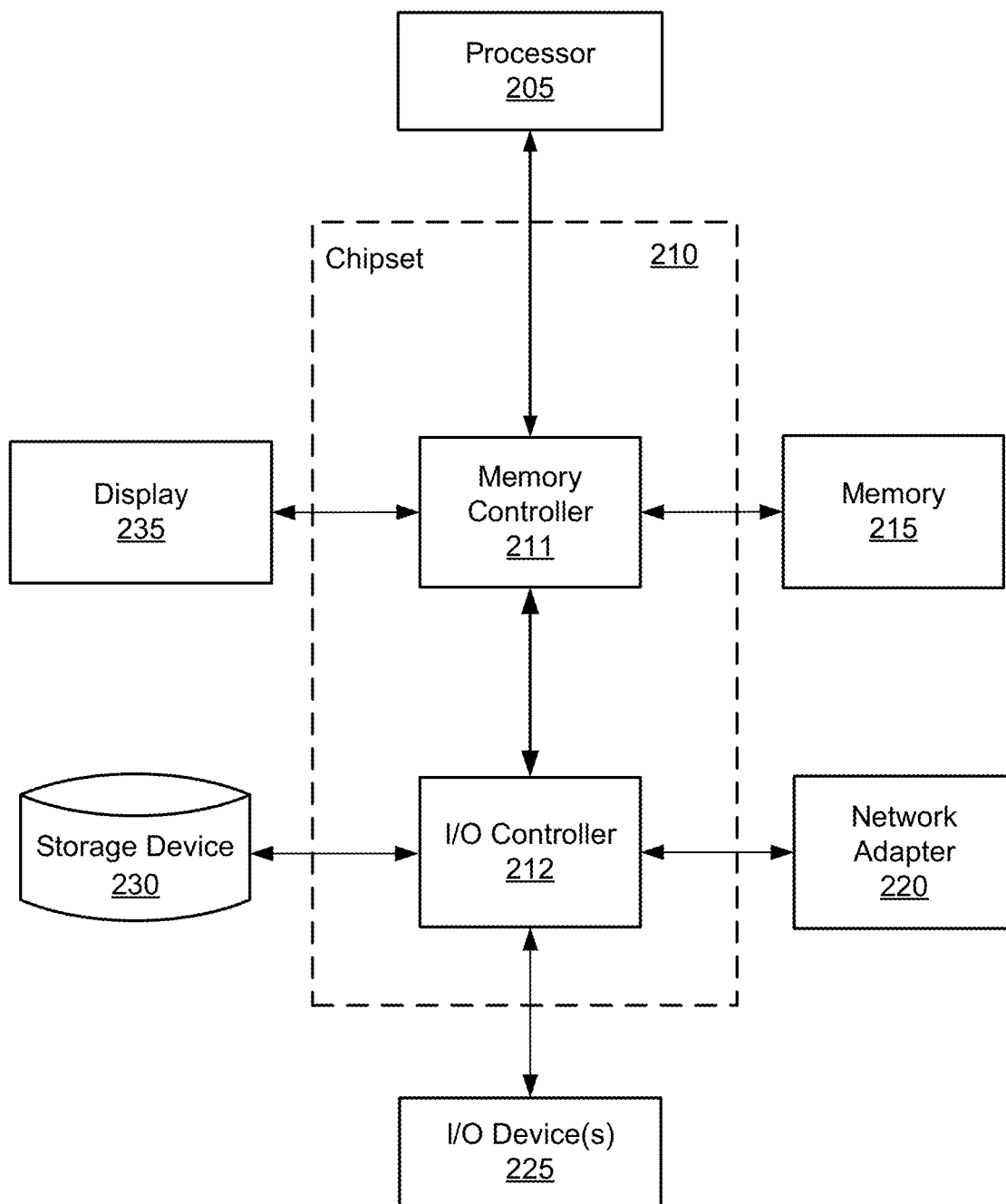
FIG. 2 is a high-level block diagram illustrating an example of a computing device used in either as a client device, application server, and/or database server, according to one embodiment.

FIG. 2 is a high-level block diagram illustrating physical components of an example computer 200 that may be used as part of a client device 110, application server 130, and/or database server 140 from FIG. 1, according to one embodiment. Illustrated is a chipset 210 coupled to at least one processor 205. Coupled to the chipset 210 is volatile memory 215, a network adapter 220, an input/output (I/O) device(s) 225, a storage device 230 representing a non-volatile memory, and a display 235. In one embodiment, the functionality of the chipset 210 is provided by a memory controller 211 and an I/O controller 212. In another embodiment, the memory 215 is coupled directly to the processor 205 instead of the chipset 210. In some embodiments, memory 215 includes high-speed random access memory (RAM), such as DRAM, SRAM, DDR RAM or other random access solid state memory devices.

The storage device 230 is any non-transitory computer-readable storage medium, such as a hard drive, compact disk read-only memory (CD-ROM), DVD, or a solid-state memory device. The memory 215 holds instructions and data used by the processor 205. The I/O device 225 may be a touch input surface (capacitive or otherwise), a mouse, track ball, or other type of pointing device, a keyboard, or another form of input device. The display 235 displays images and other information from for the computer 200. The network adapter 220 couples the computer 200 to the network 150.

As is known in the art, a computer 200 can have different and/or other components than those shown in FIG. 2. In addition, the computer 200 can lack certain illustrated components. In one embodiment, a computer 200 acting as server 140 may lack a dedicated I/O device 225, and/or display 218. Moreover, the storage device 230 can be local and/or remote from the computer 200 (such as embodied within a storage area network (SAN)), and, in one embodiment, the storage device 230 is not a CD-ROM device or a DVD device.

Generally, the exact physical components used in a client device 110 will vary in size, power requirements, and performance from those used in the application server 130 and the database server 140. For example, client devices 110, which will often be home computers, tablet computers, laptop computers, or smart phones, will include relatively small storage capacities and processing power, but will include input devices and displays. These components are suitable for user input of data and receipt, display, and interaction with notifications provided by the application server 130. In contrast, the application server 130 may include many physically separate, locally networked computers each having a significant amount of processing power for carrying out the analyses introduced above. In one embodiment, the processing power of the application server 130 provided by a service such as Amazon Web Services™. Also in contrast, the database server 140 may include many, physically separate computers each having a significant amount of persistent storage capacity for storing the data associated with the application server.

As is known in the art, the computer 200 is adapted to execute computer program modules for providing functionality described herein. A module can be implemented in hardware, firmware, and/or software. In one embodiment, program modules are stored on the storage device 230, loaded into the memory 215, and executed by the processor 205.

III. Dashboard

Figure 3A:
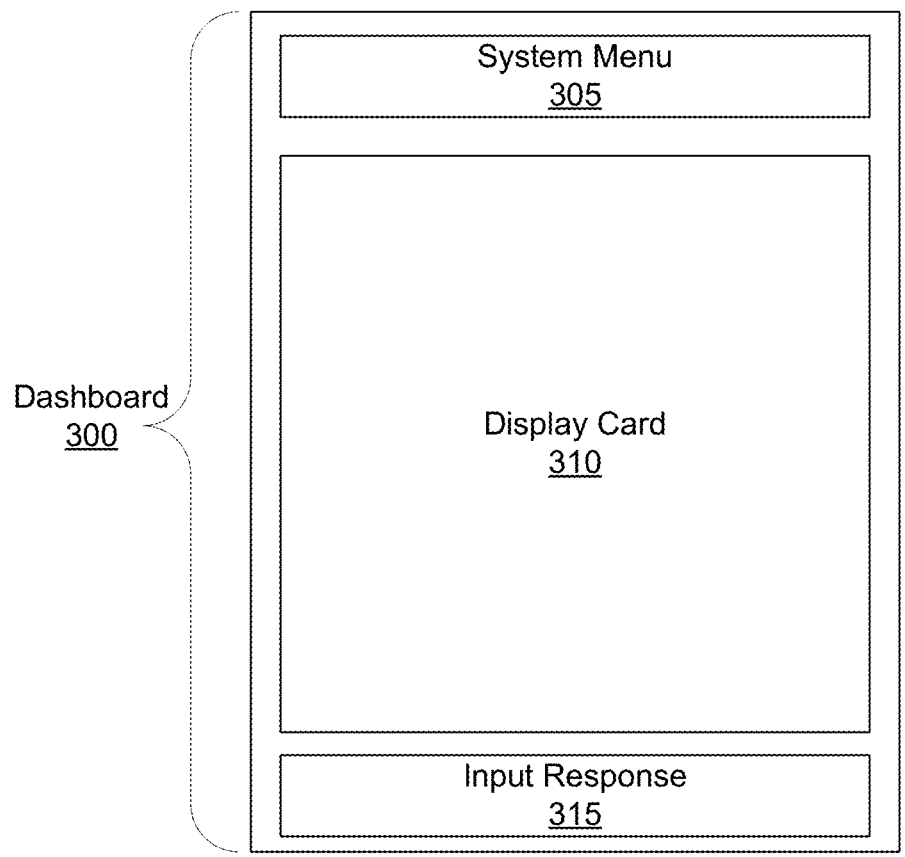
FIG. 3A shows a dashboard of a client application that allows a user to interact with an analytics system, according to one embodiment.

The dashboard, for example dashboard 300 illustrated in FIG. 3A, allows users to interact with the analytics system 100. The dashboard 300 provides a means to transfer information on a user-to-user (e.g., patient 111 to provider 112) or user-to-system/system-to-user basis. Dashboards 300 are accessed through the client application 115 on the client device 110 and provide a mechanism for both patients and healthcare providers to monitor medication rescue events, exchange personalized patient healthcare information, and received notifications. Patients may communicate with other health care provider and other patients through the dashboard 300, for example, to discuss and share information about their condition, medication usage, and management. The ability to share healthcare information may give patients or healthcare care providers experiencing a same issue a way to share individual perspectives.

The dashboard 300 also allows authorized health care providers 112 to access a list of patients to view, annotate, update, interact with, and export information about patient and community data and statistics in various demographics or geographic segments. Using the dashboard 300, healthcare providers are able to monitor patients individually or in aggregate, to receive and provide feedback (e.g. compliance reminders) on how their associated patient populations are responding to medication and condition management guidance. A healthcare provider who has access to individual or multiple patients has the ability to establish notification thresholds, set parameters for the notifications, and receive notifications when patients' event history matches certain conditions (e.g., a rescue event). Additionally, the dashboard 300 can receive and display regular reports of event patterns for specific demographic generated by the analytics system 100.

The dashboard 300 presents a variety of information including tabular data, graphical visualizations, and analyses to users through display "cards" 310. Display cards 310 are conformably suited to smaller displays typical of portable client devices 110, for example mobile phones or tablets, and include "bite size" pieces of information that mimic the simplistic organizational style found in baseball cards. The dashboard 300 may also include a system menu 305 that allows users to navigate through different categories of healthcare information.

Notifications provided by the application server 130 are related to the display cards 310. Generally, notifications include not only information to be presented to the user through the application 115, but also parameters for specifying which display card 310 is to be used to display the contents of the notification. Generally, any information pushed/pulled from the application server 130 may be associated with one or more cards. For example, a notification can be pushed to the patient based on the outcome of an analysis performed by server 130. The dashboard 300 will process the notification and determine which card/s to use to present the information in the notification. Continuing the example, the recipient of the notification may make a request (pull) data from the application server 130. The application server 130 provides the requested data in another notification, and the dashboard 300 then determines which display card 310 to display the requested information.

To interact with information presented, some display cards 310a include a input response 315 area. For example, in the display card 310b illustrated in FIG. 3B, a patient may scroll up or down in the input response 315 area to select a controller medication used to manage COPD or select the "next" to move to an additional display card 310.

Figure 3B:
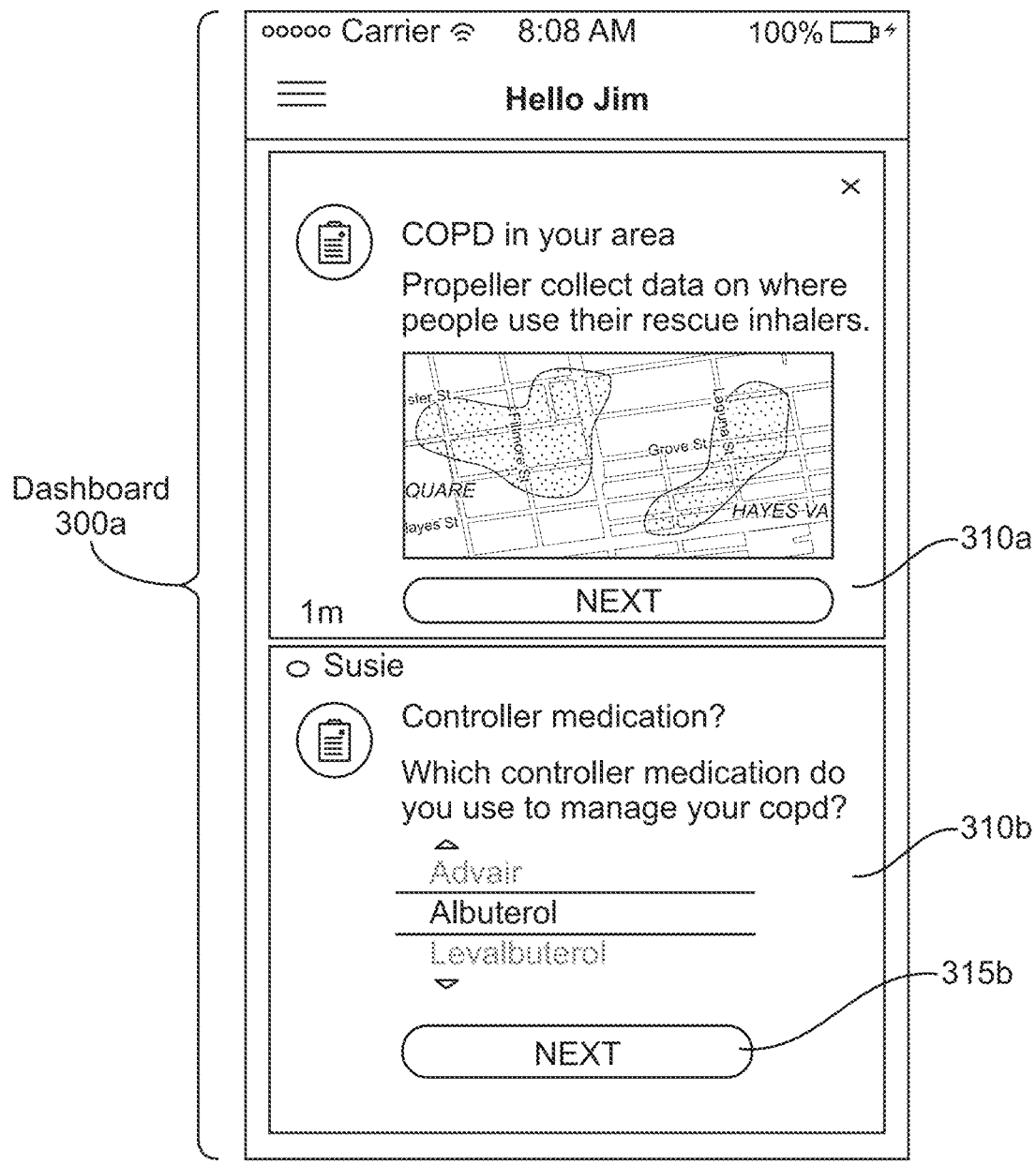

The dashboard 300 may provide a variety of different display cards 310, which may be organized into categories. A single display card 310 may fall into one or more categories. An information card type includes non-actionable cards that merely display data. Information cards may, for example, medication usage events, statistics, and maps including both patient data and community data. Information cards are further sub-categorized into event and trend display cards. Event cards include data relating to controller and rescue medication events, such as a list of historical medication rescue events for a specific patient, or patient rescue event data overlaid on a geographical map for a specific provider. For example, the display card 310a illustrated in FIG. 3B is an event card that highlights patients experiencing COPD rescue events in a particular geographic area.

Figure 3C:
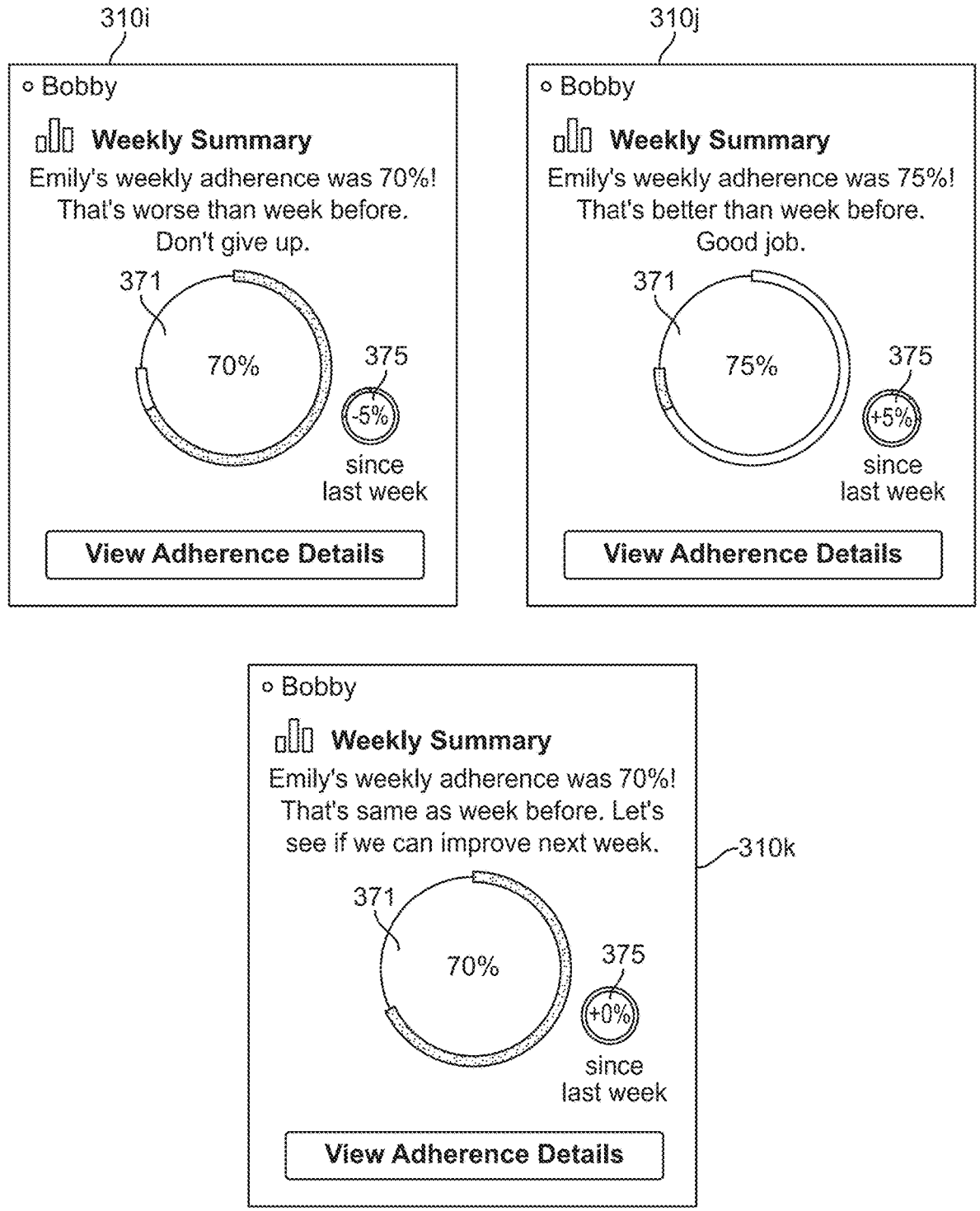

A trend card include statistical information presented using a graph or a chart designed for clear comprehension by the recipient. Trend cards may include an analysis based on one or more types of information over one or more time periods. For example, trend cards may illustrate line or bar charts that summarize medication usage over time periods. FIG. 3E illustrates two different example trend cards, plotting COPD rescue events 310c and COPD controller medication adherence 310d, both over various time periods. FIG. 3H illustrates a trend card 310n that shows week-over-week adherence data and trends. FIG. 3I illustrates four different example trend cards. Card 310o displays a time of day trend indicating the proportion or amount of medication events that occur during a particular time of day, card 310p displays a symptom trend indicating the proportion or amount of a patient's symptoms that are a particular symptom, card 310q displays a day of week trend indicating the proportion or amount of medication events that occur during a day of the week, and card 310r displays a trigger trend indicating the proportion or amount of a patient's medication events that are caused by a particular trigger. FIG. 3J illustrates two example trend cards. Card 310s and 310t display days with symptoms in the prior seven days, nighttime events in the prior thirty days, and an asthma control score indicator (e.g., "Still Learning" and "Well Controlled").

A survey card type solicits a user response by presenting yes/no, multiple choice, or more open-ended questions for the user to respond to. For example, a healthcare provider or the analytics system 100 may send a survey card with a COPD questionnaire to a patient 111 to determine a level of disease control for a specific patient. As an additional example, a survey card may request the type of controller medication that the patient 111 uses to treat COPD symptoms, as shown in the display card 310b illustrated in FIG. 3B. Generally, survey cards provide the application server 130 with data that may be missing from a patient's medical history or patient profile (as introduced above), and/or provide an update to possible outdated information. Generally, one or more survey cards may be used to complete the patient enrollment process and create a patient profile for storage in database server 140. As a specific example, when a patient 111 initially enrolls in the analytics system 100, a push notification will be triggered by the application server 130 prompting the patient 111 to create a patient profile. Example of survey cards are illustrated in FIGS. 3F, 3G, and 3K, which illustrate a survey question asking whether pollen is a COPD trigger 310e, what the patient's controller medication is 310f, how many times the patient used their rescue medication to control an event 310g, what their controller medication daily schedule is 310h, and how often asthma has kept the patient from getting things done in the last four weeks 310u. Survey cards may also ask about a patients asthma triggers. Other survey cards ask a patient to rate their general quality of life on 5-point Likert scale, to rate their quality of sleep, to rate their ability to be active over last 7 days, and so on. Other survey cards ask whether the patient feels better or worse than yesterday, whether the patient has had to go to emergency room or hospital in last 12 months for an exacerbation and so on.

In some instances, patient behavior or sensor-reported event information that is inconsistent with existing patient information may trigger the sending of a survey card in order to resolve ambiguity as to the patient's circumstances. For example, if the patient is experiencing a greater-than-expected count of COPD events, the survey card may request information about the type of medication the patient is currently using as listed on their medicament device 160, in order to verify that the correct medication is being used. As another example, if the reported information about controller medication use indicates that the patient is only using the controller medication one time per day but their adherence plan indicates they are supposed to be taking their controller medication twice per day, system 100 could send a notification asking if the patient needs to change their adherence plan. FIG. 3L illustrates an example survey card 310v for asking whether a patient wants the time zone associated with the patient's profile to be changed based on detecting a different time zone associated with a client device 110. The survey card 310v includes an input response area 315d that may automatically update the profile time zone or navigate to a different screen in the user interface for changing the profile time zone.

Navigation cards represent actionable data or messages that, upon user interaction, may redirect the user to another screen or card that is part of the dashboard 300. For example, if a patient wants to share information or request specific medication plans for controller medications with a physician, a navigation card would be used to facilitate the sharing of information or enrollment in controller adherence plan. Additionally, navigation cards allow users to update information surrounding medication rescue events. For example, the card of FIG. 3H includes input response area 315c to view adherence details. Selecting button 350 redirects the user to the timeline illustrated in FIG. 3M, which is discussed in more detail below.

Adherence cards are designed to encourage a patient to continually use their controller medication on schedule over different periods of time. FIGS. 3C and 3H illustrate example adherence cards. Cards 310i, 310j, and 310k are example adherence summary cards. The cards 310i-k illustrate a metric of adherence over a time period, such as proportion of doses a patient has taken over the last week. The cards 310i-k may also compare the metric of adherence during prior time periods (e.g., last week) to illustrate a trend in adherence. The cards may include a graphical indicator of the adherence metrics. In card 310i, the patient's weekly adherence is 70%, as shown by the darker line that extends around 70% of the circular indicator 371. The patient's adherence the prior week was 75% as indicated by the lighter line. The smaller indicator 375 shows a percent change between the previous time period and the current time period. In card 310j, the current week's adherence is 75% while the previous week's is 70%, and in card 310k, the current week and the previous week have the same adherence of 70%. Card 310n displays week-over-week adherence data and trends. Additional example adherence cards are described below with respect to FIGS. 5A-L and 6A-I.

Figure 3D:
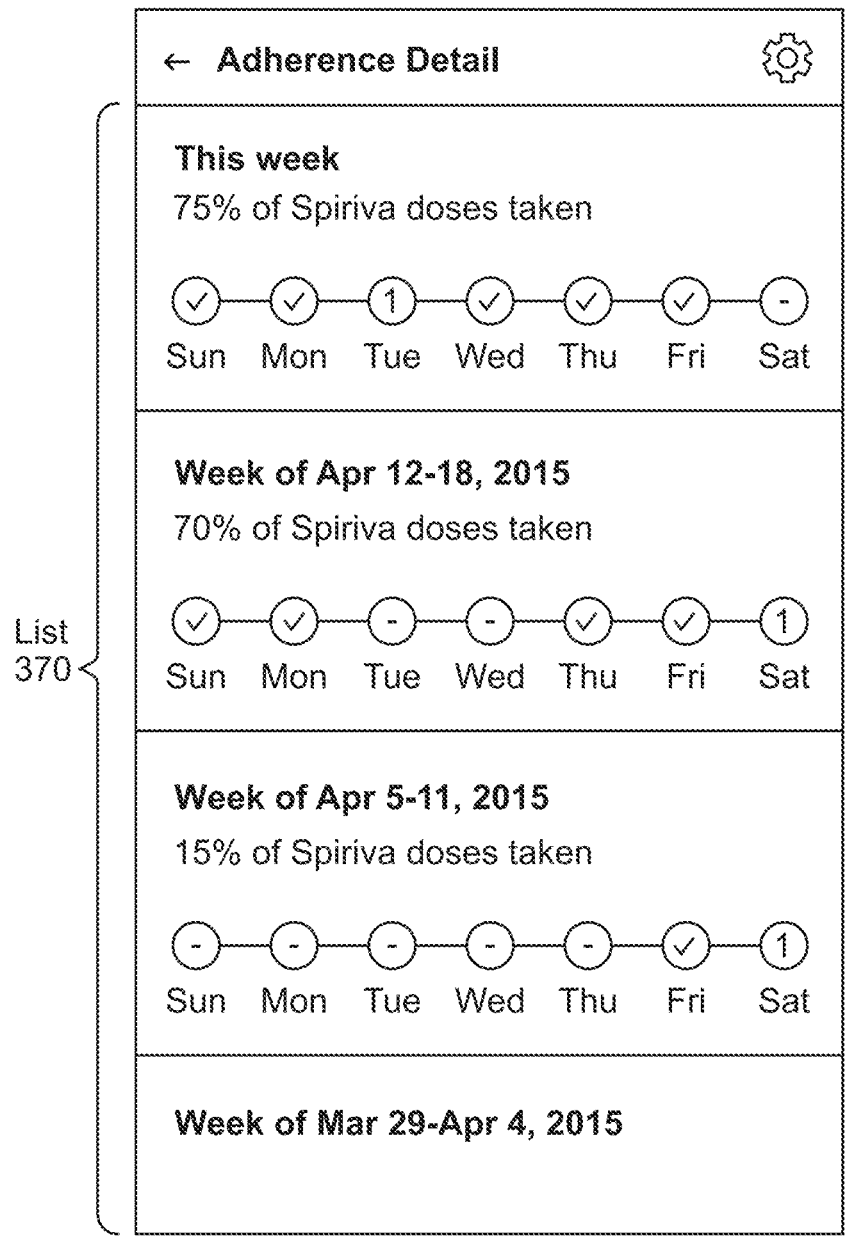
Figure 3E:
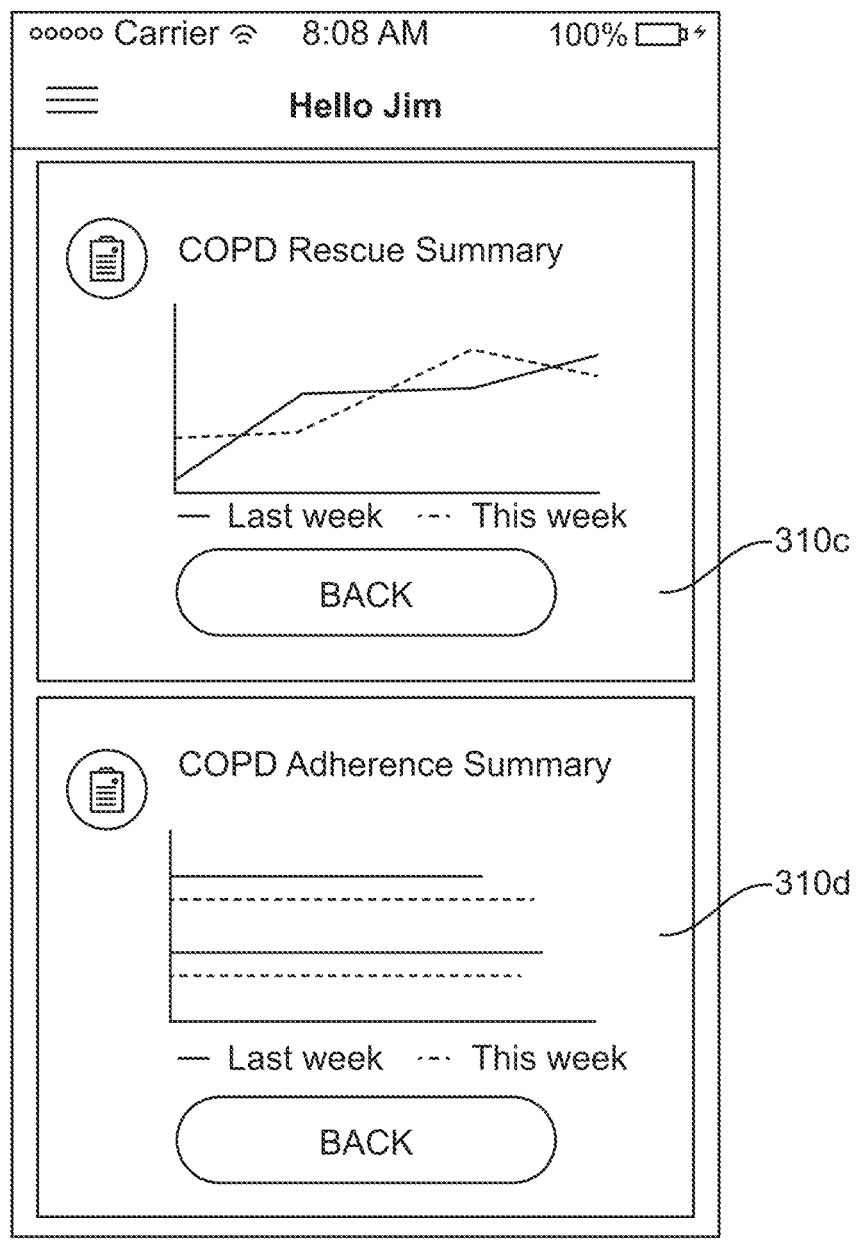
Figure 3F:
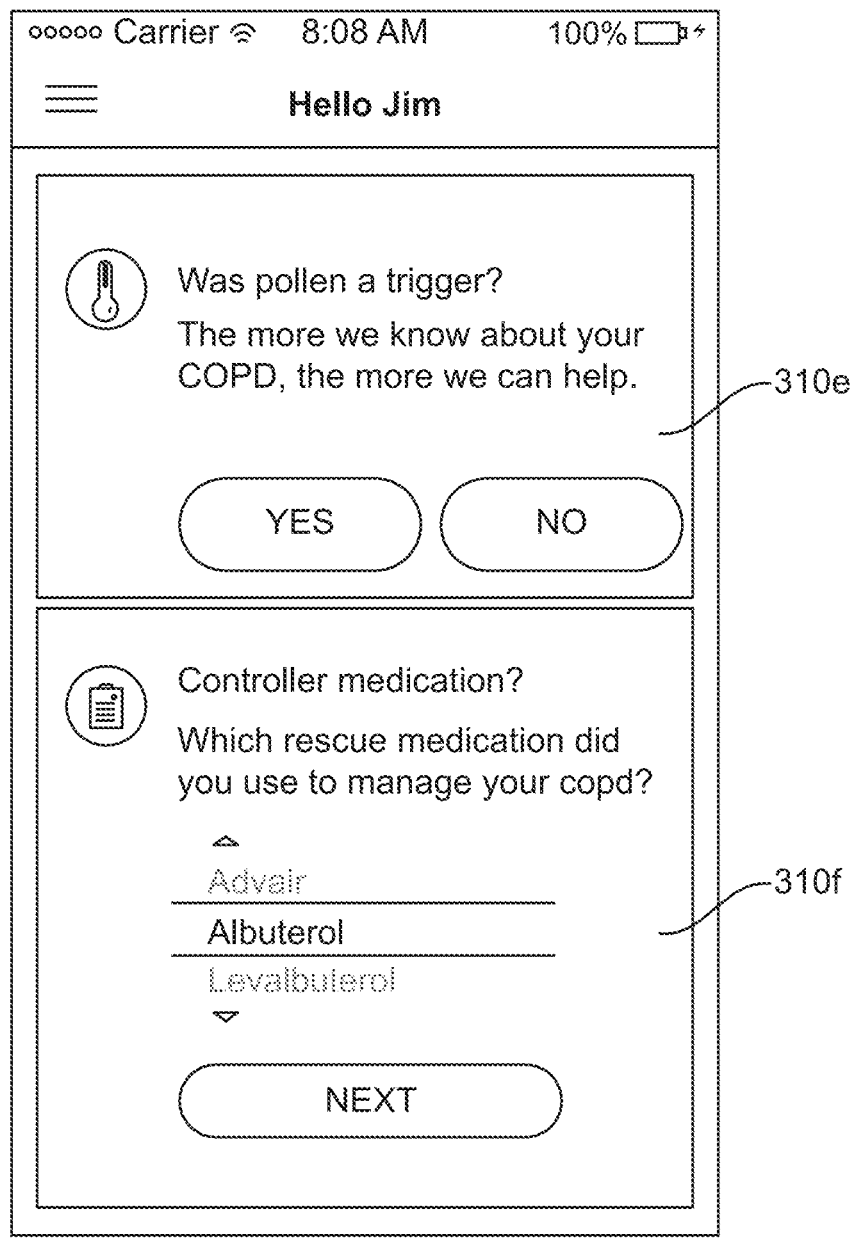
Figure 3G:
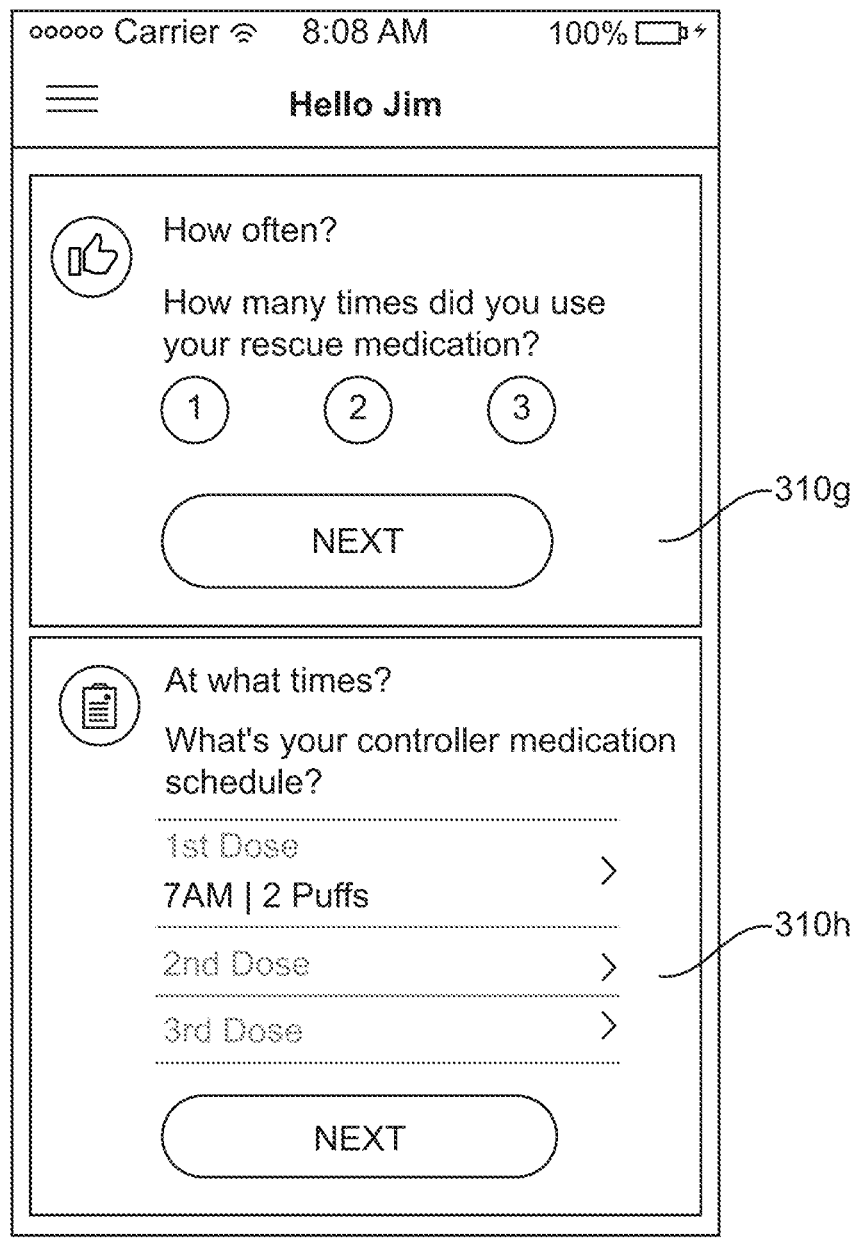
Figure 3H:
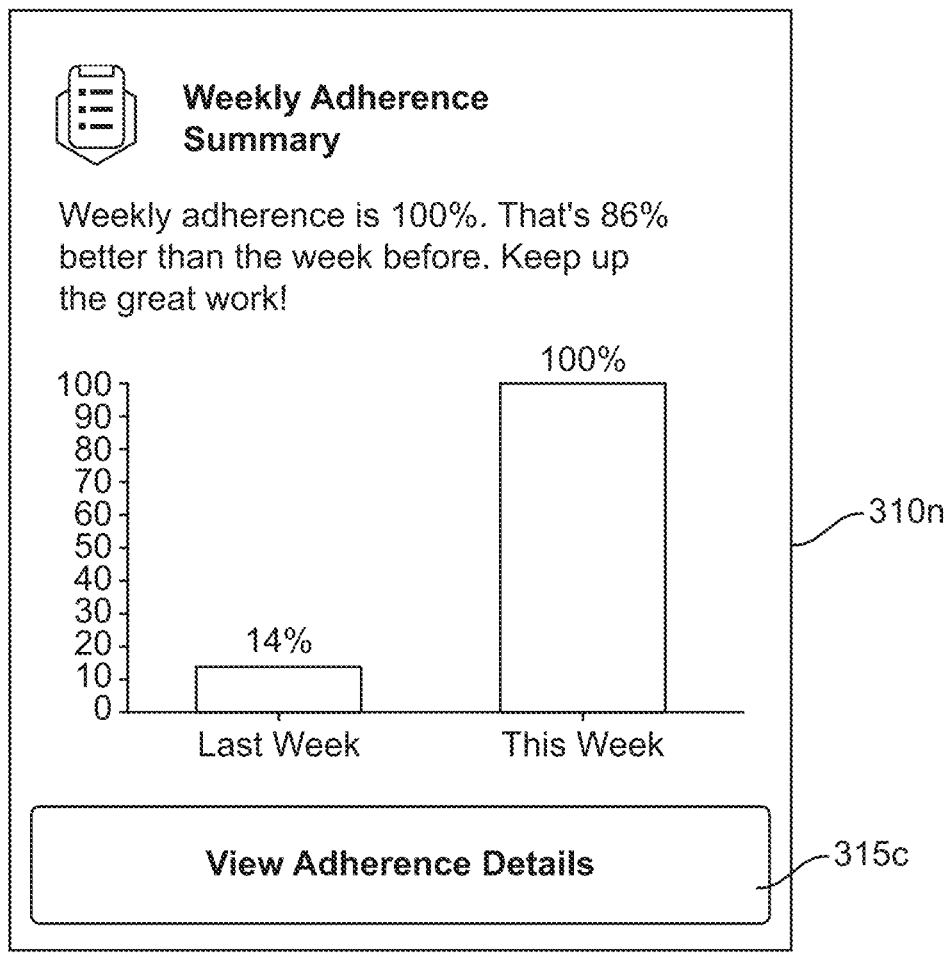
Figure 3I:
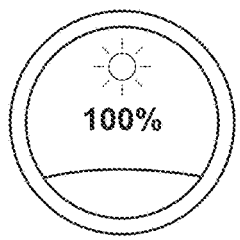
Figure 3I:
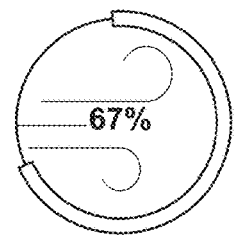
Figure 3I:
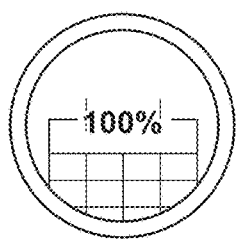
Figure 3I:
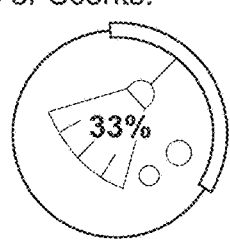
Figure 3J:
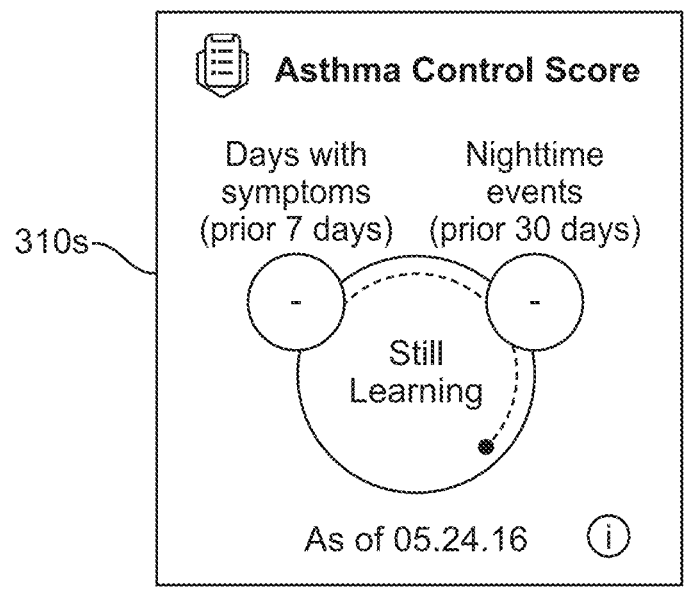
Figure 3J:
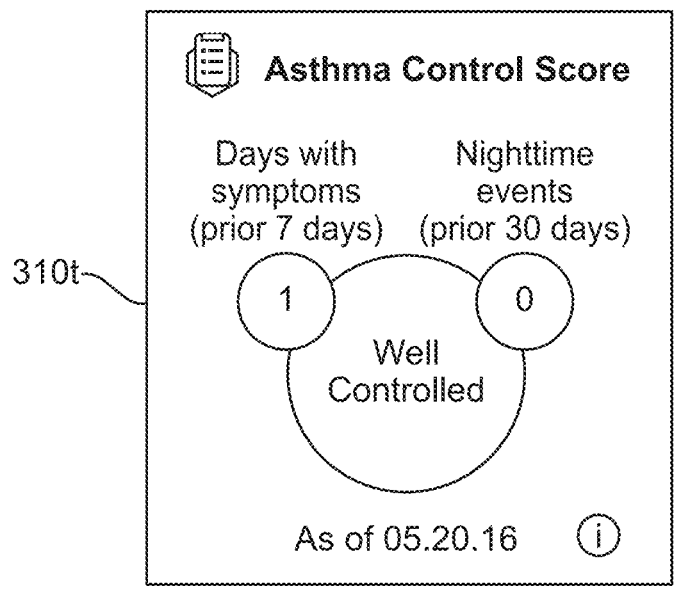
Figure 3L:
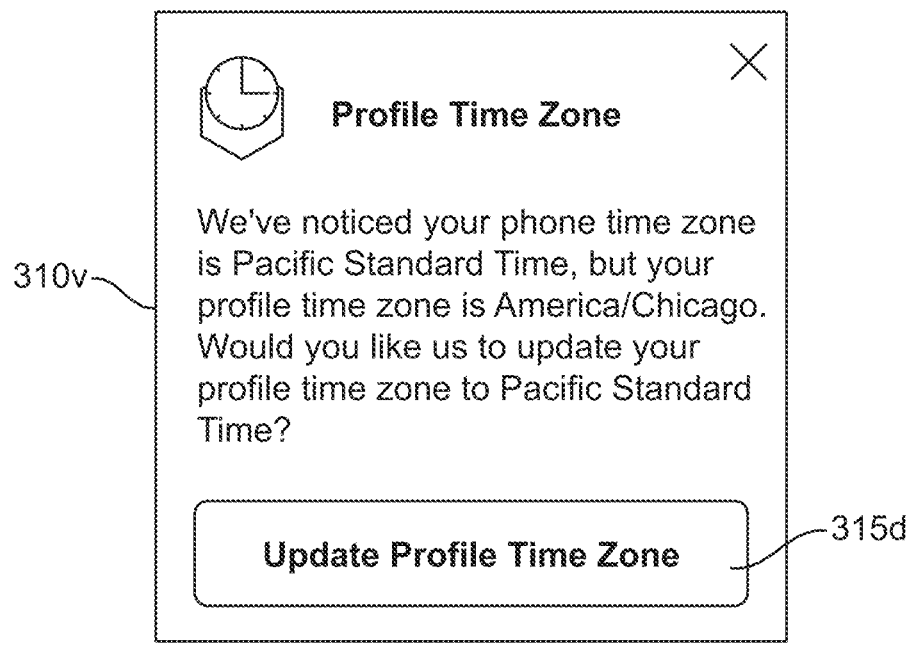
Figure 3M:
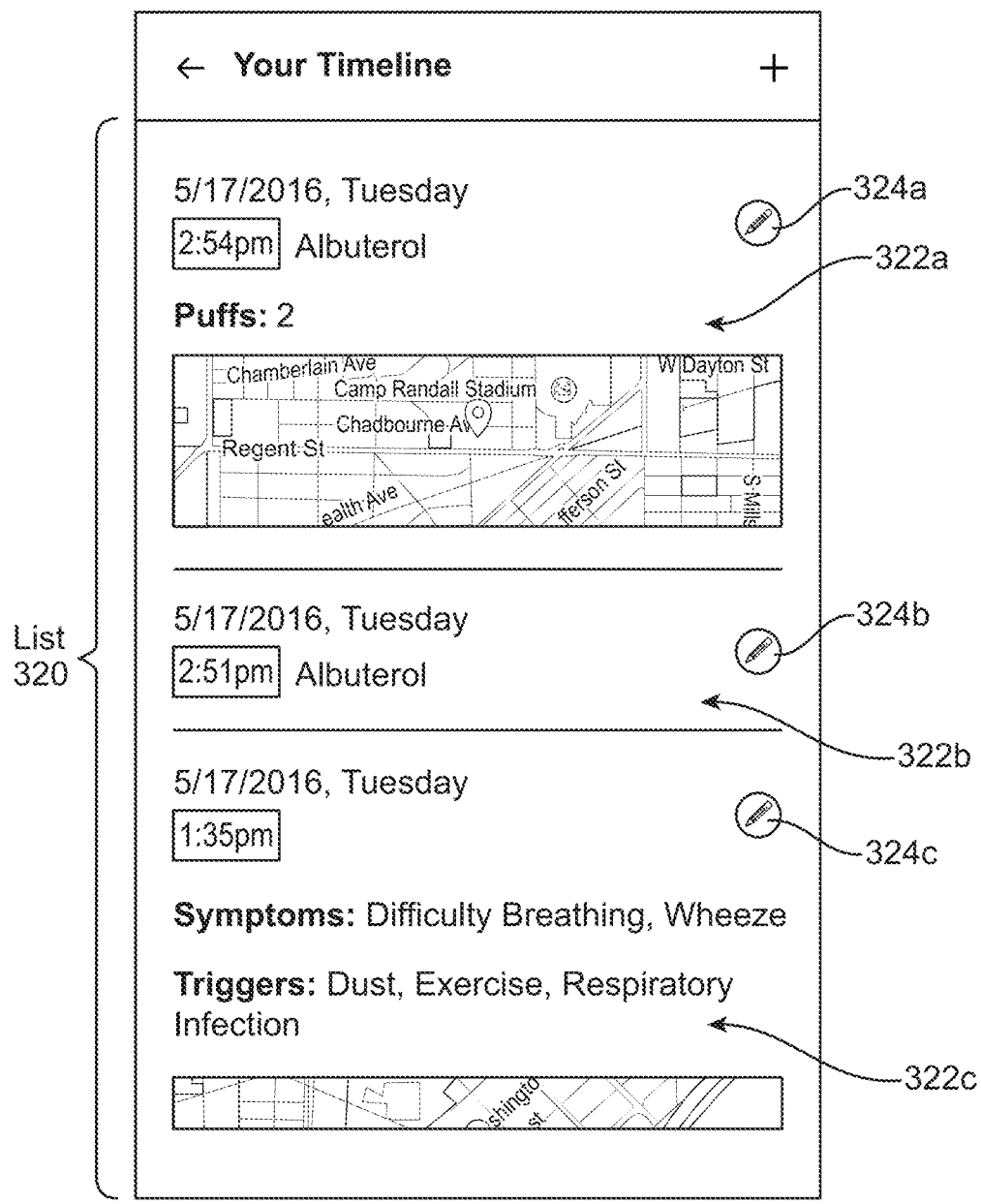
Figure 3N:
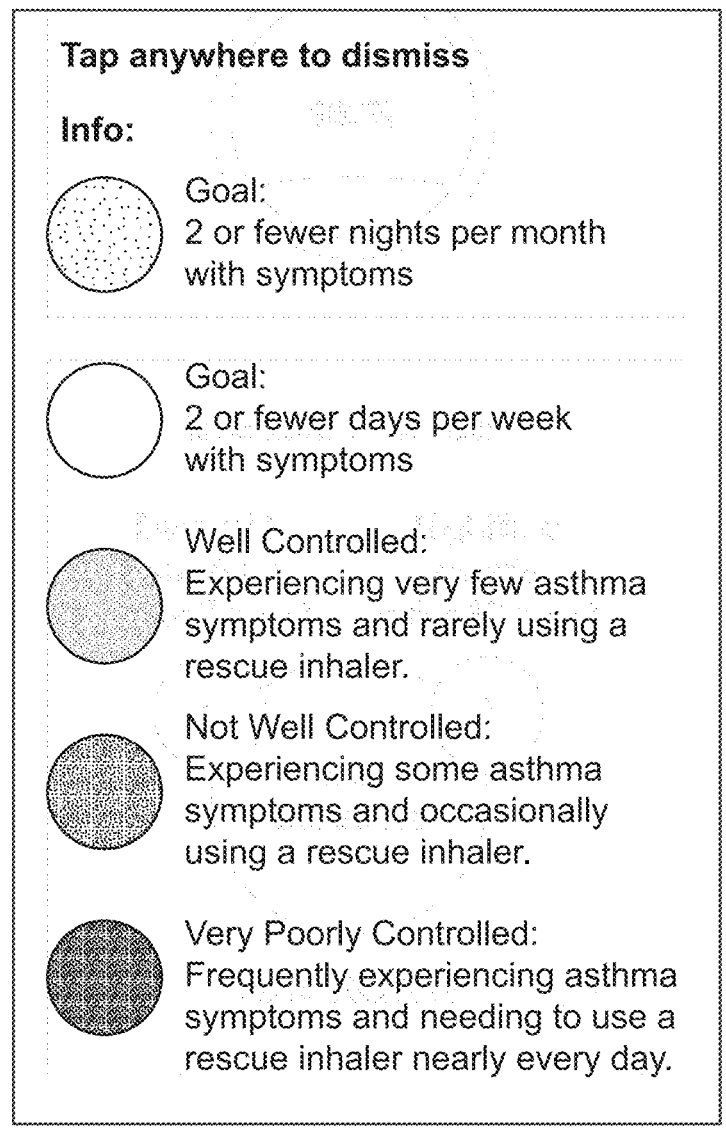

FIGS. 3D, 3M and 3N illustrates example user interfaces presented in the dashboard 300. FIG. 3D illustrates a list 370 of dose adherence details by week for a particular medication ("Spirriva"). The list entries include a time period (e.g., "This week"), a summary of the proportion of doses taken (e.g., 75% of Spirriva doses taken), and a graphical illustration of daily adherence. The checkmarks indicate that all doses were taken for a particular day, while a number indicates that some but not all doses were taken and a dash indicates no doses were taken. FIG. 3M illustrates a list 320 of controller usage events 322a-322c. The list 320 may be presented to a recipient responsive to selection of the "View Adherence" input response area 315c of FIG. 3H. Returning to FIG. 3M, the list 320 displays controller usage events over a time period and includes details such as date, time, number of puffs, and location. Recipients may edit rescue usage events and/or add additional details such as experienced symptoms and suggested triggers by selecting the edit interaction response areas 324a-d. FIG. 3N illustrates information regarding an asthma control score indicator displayed, for example in cards 310s and 310t of FIG. 3J.

IV. Event Detection Process

As an initial step for generating notifications, a patient interfaces with the dashboard 300 to 405 a patient profile. Once the patient is finished completing their patient profile, the client device 110 transmits the patient profile for use by the application server 130 and storage by the database server 140. Once a patient's patient profile is initialized, the application server 130 may begin to receive medications events, including rescue medication events and controller medication events detected by the sensor 120 associated with the patient's medicament device 160.

Figure 4:
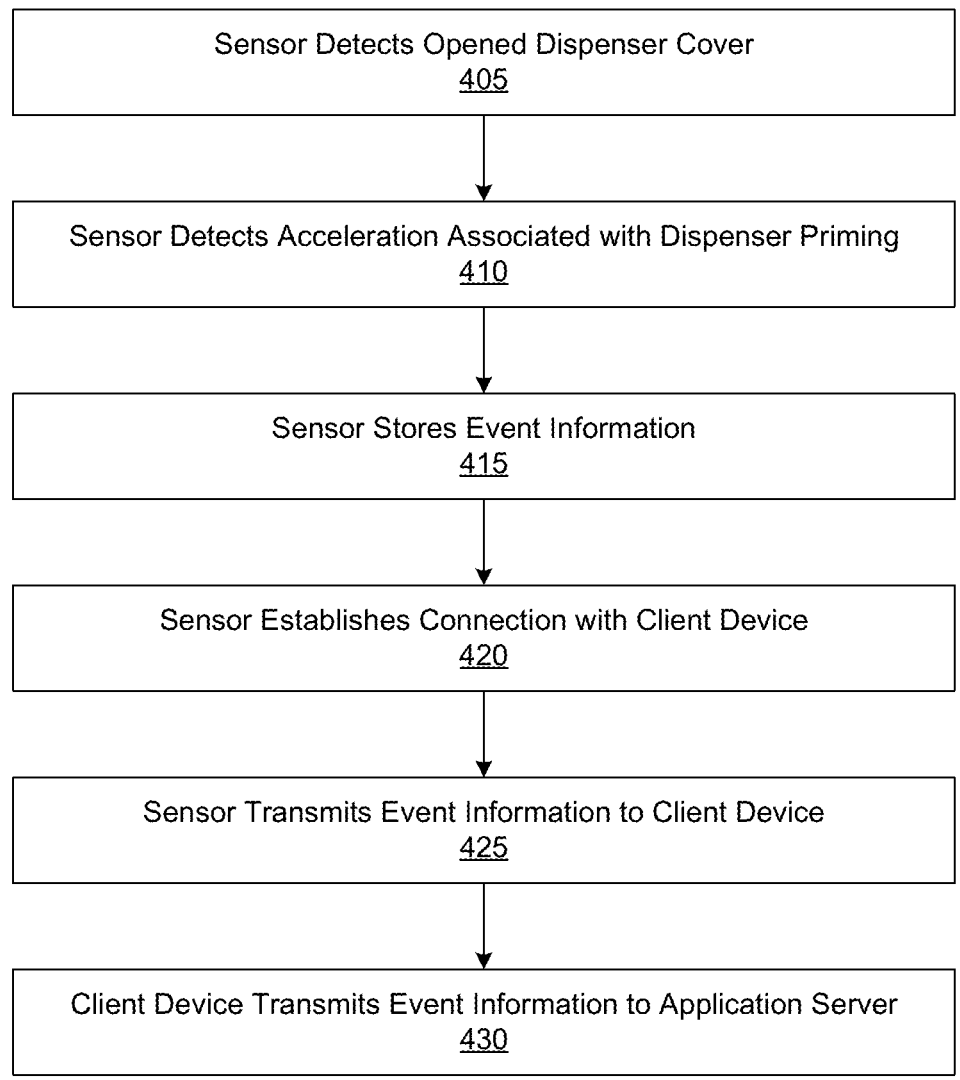
FIG. 4 shows a flowchart for detecting a medication event by an analytics system, according to one embodiment.

Referring now to FIG. 4, the application server 130 generally receives an event anytime the patient uses their rescue or control medicament dispenser 160 to relieve difficulty breathing or other respiratory symptoms. As an example of the process for capturing such an event for a particular device 160/sensor 120 combination, at the start of symptoms, the sensor 120 may detect 405 whether a medication dispenser 160 cover is opened. When the medication dispenser cover is opened, the sensor 120 may detect an acceleration 410 associated with a priming of the dispenser 160. For some types of medicament dispensers, the "priming" includes activating a mechanism to release a dose of a medication from a packaging. In other types of medicament dispensers, the "priming" includes a rapid shaking of a medication canister.

After the priming action is detected, the sensor 120 is configured to store 415 data associated with the event in active memory of the sensor 120. The event data may include information that describes the time and date of associated with the event, the status or condition of the medicament device 160 (e.g. battery level), the number of doses of medication remaining (before or after the event), self-test results, and physiological data of a patient being treated with the medicament device 160 as measured by the sensor 120. As soon as the sensor establishes a network connection with either the client device 110 or network 150, the sensor transmits 425 any locally stored event data to the client device 110 or the application server 130. If the event data was transmitted to the client device 110 first, the client device 110 then transmits 430 the event data to the application server 130 as soon as the client device 110 establishes a network connection with the network 150. Depending upon the implementation, either the client device 110 or sensor 120 will add the geographic location where the event took place to the event data transmitted to the application server 130.

V. Controller Medication Dosing Notifications

One type of analysis performed by the data analysis module 131 is to analyze controller medication usage events (i.e., doses taken by the patient) recorded by the application server 130 as reported by the client device 110, sensor 120, and/or medicament device, in order to provide notifications to the patient that both report historical information about the events, and also to provide recommendations about whether and when to take their next dose. These recommendations are also determined based on the controller medication plan set up by the patient 111 or their healthcare provider 112.

V.A. First Embodiment

Figures 5A, 5B:
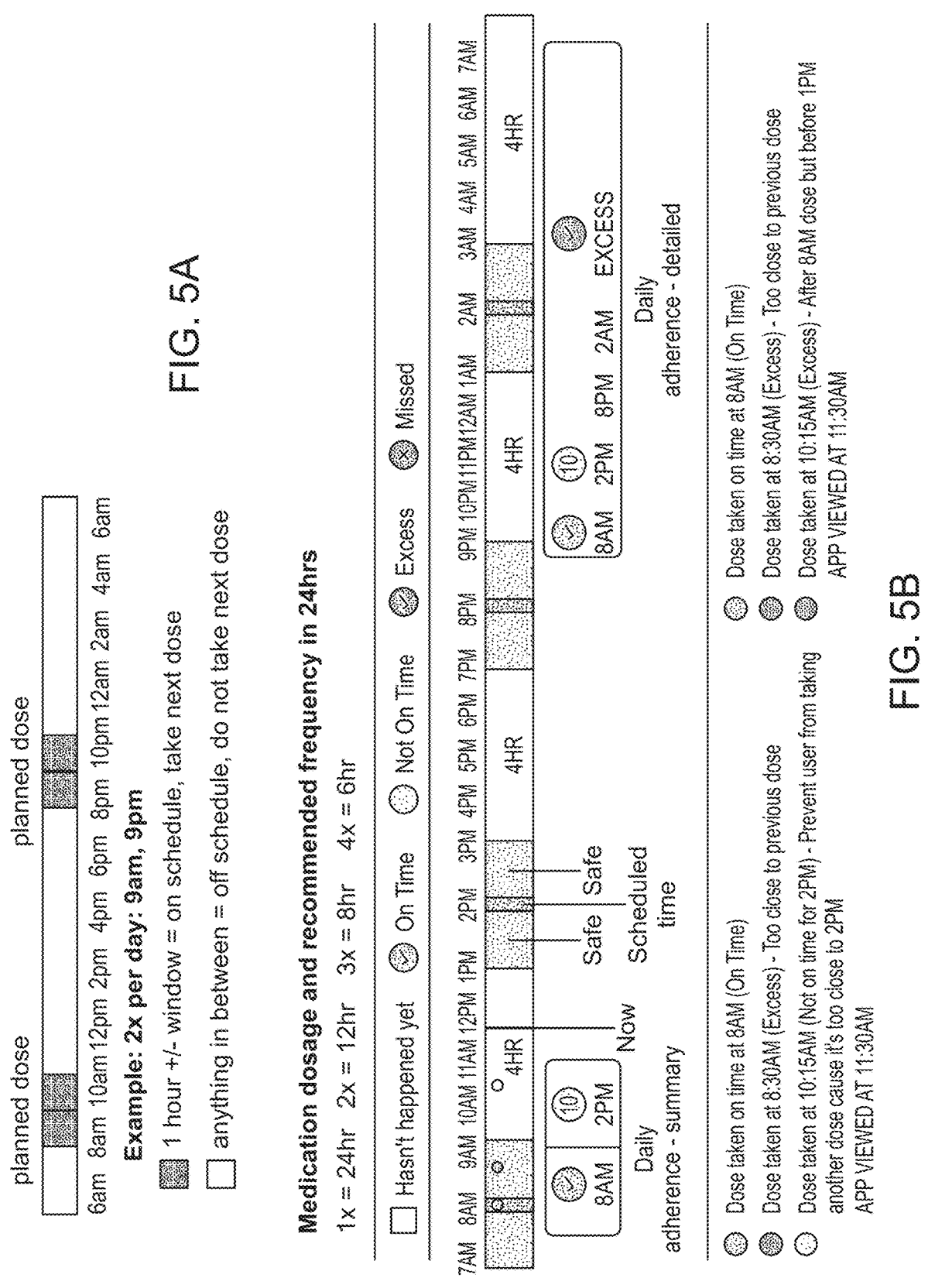

FIG. 5A illustrates an example timeline of a first embodiment for determining whether to recommend that the patient take their next dose, as may be included in a notification sent to the patient's device 110. In the first embodiment, a multi-hour hour "narrow" window around a patient's planned dose (e.g., two hour window, one hour before plan time and one hour after plan time) is used to evaluate whether to recommend that the patient take a dose of controller medication. If a patient takes a dose after their plan time, but inside the narrow window, then the data analysis module 131 will still remind the patient to take the next dose. For example, if the patient's plan time is 9 am, and they take the dose at 9:59, then the data analysis module 131 will still remind them to take the next dose (9 pm).

Alternatively, if the patient takes a dose outside of the narrow window, the data analysis module 131 will not remind the patient to take the next dose. For example, if the patient's plan time is 9 am, and they take the dose at 10:01, then the data analysis module 131 will not remind them to take the next dose (9 pm). If the patient's plan time is 9 am, and they take the dose at 12 pm, then the data analysis module 131 will not them to take the next dose, etc.

This is a coarse solution. Historical data estimates about 40% of current usages may fall outside of the narrow window around planned dose time. Consequently, this implementation will stop reminding patients to take the next dose in up to 40% of cases. However, a benefit of this solution is that it is very conservative. Reminding a patient to take a dose they should not take can pose a problem for patient safety issue. This solution biases against reminding a patient to do something that could lead to a them taking an overdose and experiencing an adverse event.

FIG. 5B illustrates an example of the timeline of the first embodiment for a dosing plan that specifies that a dose is to be taken four times a day. In this example, a first dose is taken at 8 am and is registered by module 131 as on time. Another dose is taken at 8:30 am and is registered as an excess dose as it was taken too close in time to the previous dose. Another dose is taken at 10:15 which is also too early in time to be registered as the 2 pm dose, and thus is also registered as an excess dose.

Assume for sake of example that the software application associated with the server 130 was viewed by the patient 111 on their client device 110. In this instance, the module 131 may provide a notification that provides a recommendation as to whether the patient 111 should take their 2 pm dose. In this case, due to either or both of the two prior excess doses that occurred after the on time dose, the module 131 recommends that the patient skip their 2 pm dose. Alternatively, at some point prior to their 2 pm dose, for example one hour before, the module 131 may push a notification to the client device 110 with the same information.

FIGS. 5C-5G illustrate additional examples of timelines of the first embodiment for a dosing plan that specifies that a dose is to be taken twice a day. In FIGS. 5C and 5D, only a single dose is registered within a 1 hour narrow window, and thus both are registered as on time doses. In FIG. 5E, a first dose is taken within the 1 hour narrow window, and is initially registered as an on time dose. However, when another dose is closer to on time, in this case right at 9 am, the second dose is registered as the on time dose, and the prior dose is re-categorized as an excess dose as it was taken further in time from the planned dosing time.

In FIG. 5F, a first dose is taken within the 1 hour narrow window and is registered as an on time dose. Another dose taken later within the narrow window and also not sufficiently close in time is registered as an excess dose. In this case, since neither the first nor the second dose was on time or close to on time, the first registered dose is given the designation of on time. Another dose taken at 10:30 am is registered as excessive. Yet another dose is initially registered as excessive at 5 pm. At some point in time before the planned 9 pm dosing, or in response to the patient 111 checking the software application associated with the server 130, the module 131 provides a notification indicating that the patient 111 should skip the 9 pm dose due to any one or more of the previously registered excess doses. If the patient 111 follows the instructions then the 5 pm excess dose is re-categorized as merely being a not on time dose, as this dose now represents the dose that is substituting for a more on-time dose that hypothetically could have been taken closer to the planned 9 pm dose time. However, as illustrated by FIG. 5G, if the patient 111 does not view or ignores the notification provided by module 131 and instead chooses to take a dose closer to the planned 9 pm dose time, such as at 7:30 pm, then the 5 pm dose remains registered as an excess dose and the 7:30 pm dose is registered as a not one time dose, representing that it is the dose that is the best substitute for the planned 9 pm dose.

Generally, these examples represent that the categorization of a dose is not fixed in time or upon registration, but instead that categorizations shift based on subsequent controller medication events reported to the server 130.

The lengths, times, and relative positions of the time windows described in FIGS. 5A-5G are shown as examples for illustration. In practice, the time windows, dose characterization and other characteristics of the examples above can be adjusted to apply to different adherence schedules with different dose times, dose frequency, and time windows based on drug characteristics, provider input, and other considerations.

Figure 5H:
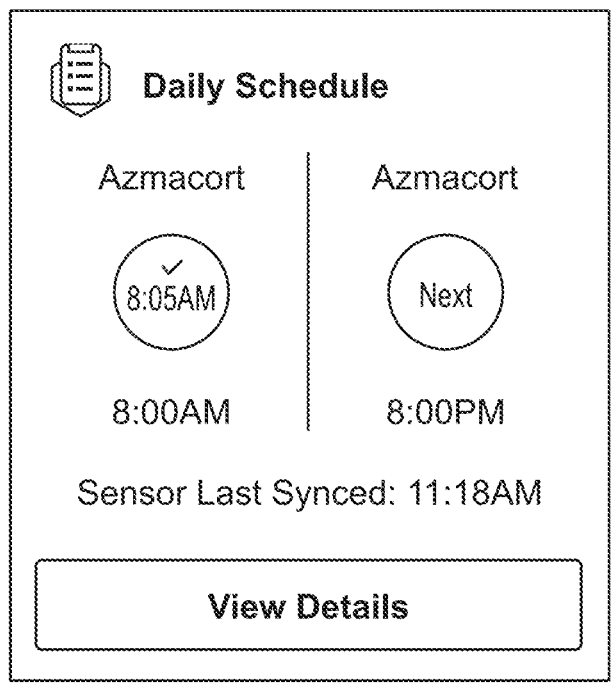
FIGS. 5H-5L illustrate example display cards that may be presented as part of notifications in accordance with this first embodiment.

FIGS. 5H-5L illustrate example display cards 310 that may be presented as part of notifications in accordance with this first embodiment. In the example of FIG. 5H, a separate listing is illustrated for each dosing planned for that day, in this case two separate dosings of Azmacort. Color coded graphics indicate whether a dose was taken that is registered for that planned dosing and what time it was taken (8:05 AM), whether it was on time (using e.g., color or pattern), whether it is still planned to be taken in the future based on the time of viewing of the notification ("Next" in circle), and when the last time the client device 110, sensor 120, and/or medicament device 160 synched with the server 130 to establish whether the information presented in the notification is current for the user ("Sensor Last Synced: 11:18 AM"). The example of FIG. 5H indicates that the dose scheduled for 8:00 AM was taken on time at 8:05 AM, and the next dose is scheduled for 8:00 PM.

Figure 5I:
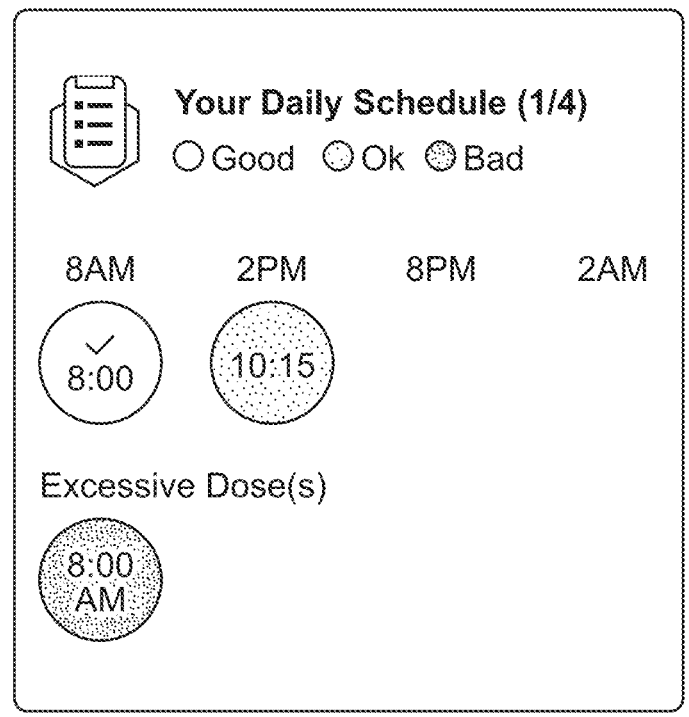

In the example of FIG. 5I, the colors correspond to the dose status, meaning whether the a dose was on time (good), off schedule (ok), or excessive (bad). In another embodiment, the dose status is indicated by different patterns, shapes, or other methods. Similarly to FIG. 5H, the planned dosing are each illustrated. Excessive dosings may be illustrated as separate graphical icons in addition to the planned dosings, along with when they were taken.

Figure 5J:
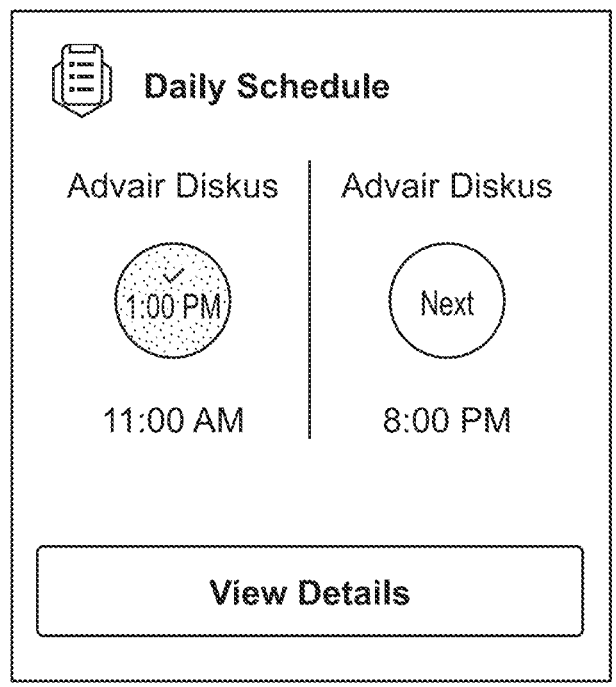
Figure 5K:
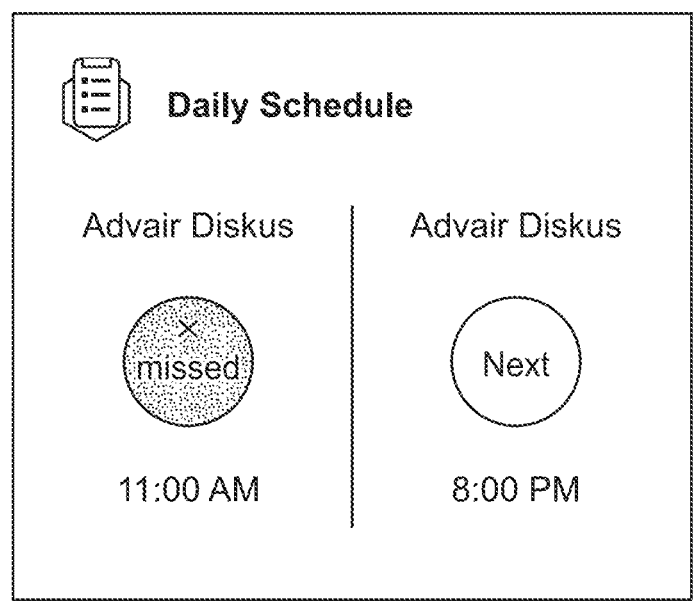
Figure 5L:
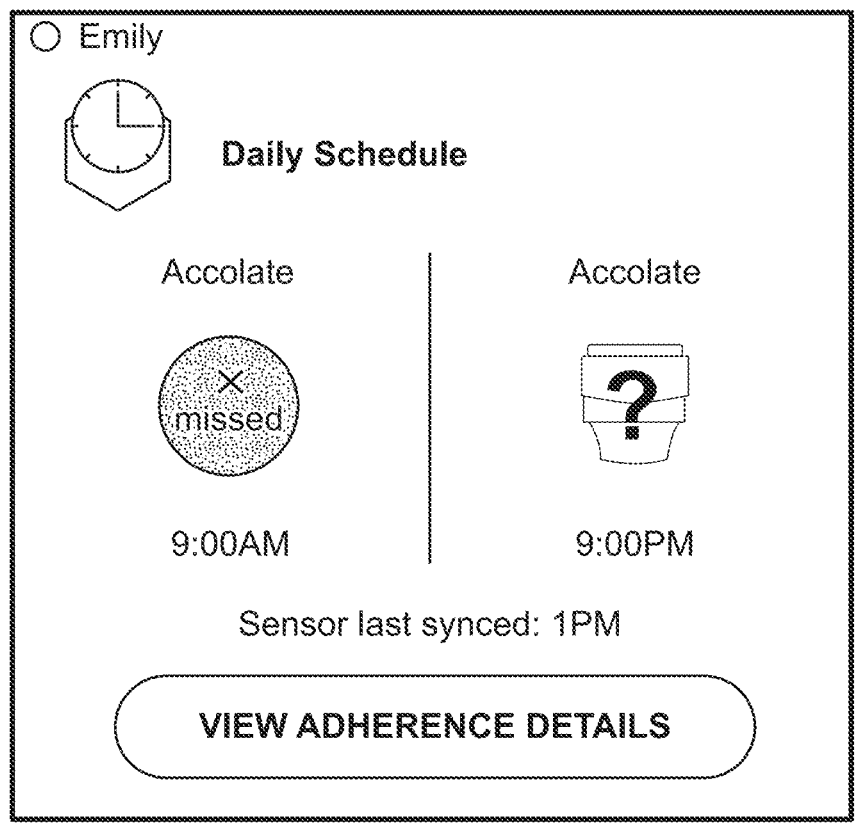

The example display card of FIG. 5J is similar to the card of FIG. 5H, however, the medication is different (Advair Diskus) and the 11:AM dose was taken late at 1:00 PM, as indicated by the color. The example display card of FIG. 5K illustrates a missed dose at 11:00 AM. The example display card of FIG. 5L illustrates a situation in which the sensor has not been synced after the scheduled time of the last dose. In the example of FIG. 5L, there is a first missed dose at 9:00 AM and an unknown status of the second dose at 9:00 PM.

V.B. Second Embodiment

Figures 6A, 6B:
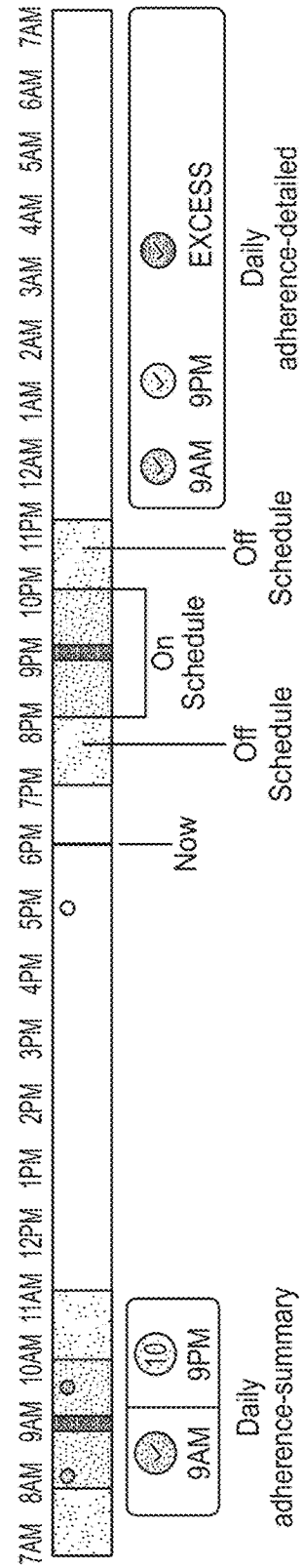
FIG. 6A illustrates a second embodiment for determining whether to recommend that the patient take their next dose, as may be included in a notification sent to the patient's device.
FIG. 6B illustrates an example of the timeline of the second embodiment for a dosing plan that specifies that a dose is to be taken two times a day.

FIG. 6A illustrates an example timeline of a second embodiment for determining whether to recommend that the patient take their next dose, as may be included in a notification sent to the patient's device 110. In a second embodiment, an expanded window around planned dose time is also used to determine whether to recommend that the patient take their next dose of controller medication, and categorize and log each previous dose event. This expanded window may be used alone, or in combination with the narrow window from the first embodiment described in the prior section. This expanded window will be based on the dosing schedule of the controller medication (e.g., one dose per day, two dose per day, etc.). The dosing schedule of a drug is based on the pharmacokinetic (PK) profile of the drug, which can be illustrated as a curve, and which represents the concentration of the drug in blood as a function of time, which thereby provides information about how quickly it is eliminated from the body. Typically one dose per day drugs have longer curves, meaning that they stay in body longer, so you only need to dose once per day. Drugs that have to be dosed more frequently (two doses a day, four doses a day, etc.) have shorter curves, meaning that they are eliminated more quickly from the body.

Several categories are defined for usage events corresponding to prior doses. If a time associated with the usage event indicates that the patient took a prior dose within the narrow window defined in the previous embodiment, then that dose is registered as an on schedule dose, under the assumption that it was taken close in time to the planned dosing time. Generally, an on-schedule prior dose will contribute to the data analysis module 131 generating a notification that recommends that the patient should in fact take their next dose.

If a time associated with the usage event indicates that the prior dose was taken outside the narrow window but within the expanded window, then the dose is registered as an off schedule dose (or more specifically as a first type of off schedule dose), under the assumption that it was not taken at an ideal time from a pharmacokinetic standpoint, but sufficiently close in time to the planned dosing time to be effective. Generally, an off-schedule dose of this type will also contribute to the data analysis module 131 generating a notification that recommends that the patient should in fact take their next dose.

If the prior dose was taken outside both the narrow and expanded window, then the dose is registered as an off schedule dose (or more specifically as a second type of off schedule dose. Generally, an off-schedule dose of this type will contribute to the data analysis module 131 generating a notification that recommends that the patient should not take their next dose, under the assumption that the prior dose was too close in time to the prior dose. This helps the data analysis module 131 avoid recommending additional doses that might trigger an overdose event.

FIG. 6B illustrates a first example of the timeline of the second embodiment for a dosing plan that specifies that a dose is to be taken two times a day. In this example, a six hour expanded window, three hours before or after the planned dosing time, may be assigned around the dosing time. Additionally, a two hour narrow window, one hour before or after the planned dosing time, may also be assigned around the dosing time. More specifically, if the planned dosing times are 9 am and 9 pm, the narrow windows may be 8 am to 10 am and 8 pm to 10 pm, and the expanded windows may be 6 am to 12 pm and 6 pm-12 am.

The size of the expanded window may vary depending upon the dosing schedule of controller medication. In one embodiment, the greater the number of doses per day, the shorter in time the expanded window is. For example, a single dose per day controller medication may have an expanded window that is twelve hours in time, six hours before or after the planned dosing time. A three dose per day controller medication may have a four hour expanded window, two hours before or after each planned dosing time. A four dose per day controller medication may have a three hour expanded window, one and a half hours before and after each planned dosing time.

Using the two dose per day example of FIG. 6B, if the patient takes a dose at 8:30 am and another dose at 9:30 am, the first dose will be registered as an on time dose as is was within the narrow window, and the second dose will be registered as an excessive dose. Another dose taken at 5 pm will be registered as an excessive dose if another dose is taken in closer proximity to the scheduled 9 pm dosing time (not shown), and as an off-schedule dose if no other dose is taken in proximity to the scheduled 9 m dosing time. If the software application supporting server 130 is viewed on the client device 110, for example at 5 pm, or if a notification is pushed to the client 110 device in advance of the 9 pm dosing time, then the user will be recommended to skip the 9 pm dose due to the prior excessive doses at 5 pm and 9:30 am.

As additional examples (not shown in the figures), again using the two planned dose per day example, if the patient takes a first dose at 9 am and another dose at 11:59 am, the data analysis module 131 will still remind patient of 9 pm dose. The data analysis module 131 registers the first of these doses as a good dose, and the second of these doses as an excessive dose, as over the period of the entire day, the patient will end up taking two or more doses rather than the planned exactly two doses. If the patient misses the dose at 9 am and takes a dose at 11:59 am, the data analysis module 131 will still remind the patient of 9 pm dose. The data analysis module 131 registers this single dose as an off-schedule dose, as according to the plan, If the patient takes a dose at 9 am and another dose at 12:01 pm, then the data analysis module 131 does not remind the patient of 9 pm dose. The data analysis module 131 registers the first dose as a good dose, and the second dose as an off schedule dose. If the patient misses their dose at 9 am and takes a dose at 12:01 pm, then the data analysis module 131 does not remind patient of 9 pm dose. The data analysis module 131 registers the first doses as a missed dose, and the second of these doses as an off-schedule dose.

Figure 6C:
FIGS. 6C-6G illustrate additional examples of timelines of the first embodiment for a dosing plan that specifies that a dose is to be taken twice a day.
Figure 6D:
Figure 6E:

FIGS. 6C-6G illustrate additional examples of timelines of the second embodiment for a dosing plan that specifies that a dose is to be taken twice a day. In FIGS. 6C and 6D, only a single dose is registered within a 1 hour narrow window, and thus both are registered as on time doses. In FIG. 6E, a first dose is taken within the narrow window, and is initially registered as an on time dose. However, when another dose is closer to on time, in this case right at 9 am, the second dose is registered as the on time dose, and the prior dose is re-categorized as an excess dose as it was taken further in time from the planned dosing time.

Figure 6F:
Figure 6G:

In FIG. 6F, a first dose is taken within the 1 hour narrow window and is registered as an on time dose. Another dose taken later within the narrow window and also not sufficiently close in time is registered as an excess dose. In this case, since neither the first nor the second dose was on time or close to on time, the first registered dose is given the designation of on time. Another dose taken at 10:30 am is registered as excessive. Yet another dose is initially registered as excessive at 5 pm. At some point in time before the planned 9 pm dosing, or in response to the patient 111 checking the software application associated with the server 130, the module 131 provides a notification indicating that the patient 111 should skip the 9 pm dose due to any one or more of the previously registered excess doses. If the patient 111 follows the instructions then the 5 pm excess dose is re-categorized as merely being a not on time dose, as this dose now represents the dose that is substituting for a more on-time dose that hypothetically could have been taken closer to the planned 9 pm dose time. However, as illustrated by FIG. 6G, if the patient 111 does not view or ignores the notification provided by module 131 and instead chooses to take a dose closer to the planned 9 pm dose time, such as at 7:30 pm, then the 5 pm dose remains registered as an excess dose and the 7:30 pm dose is registered as a not one time dose, representing that it is the dose that is the best substitute for the planned 9 pm dose.

The lengths, times, and relative positions of the time windows described in FIGS. 6A-6G are shown as examples for illustration. In practice, the time windows, dose characterization and other characteristics of the examples above can be adjusted to apply to different adherence schedules with different dose times, dose frequency, and time windows based on drug characteristics, provider input, and other considerations.

Figure 6H:
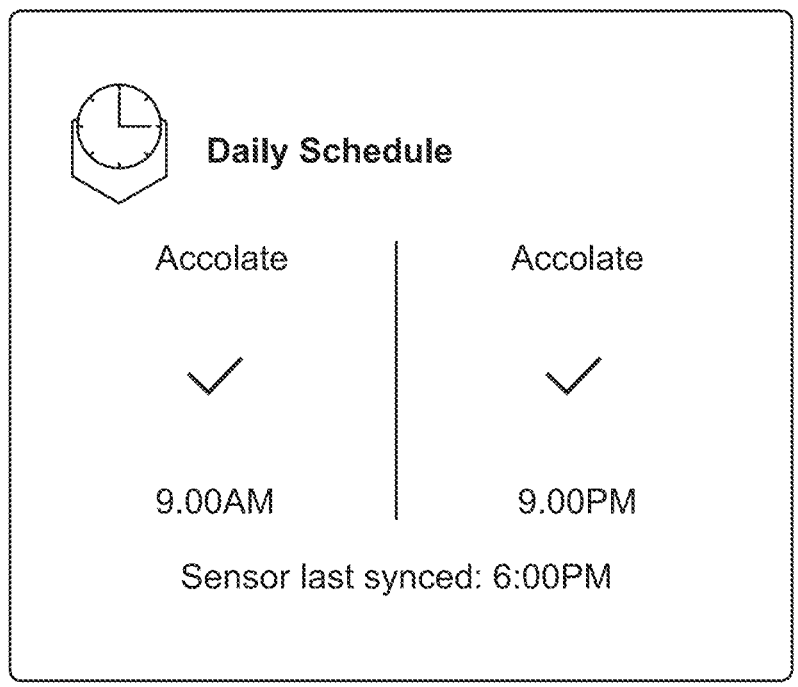
FIGS. 6H and 6I illustrate example display cards that may be presented as part of notifications in accordance with this first embodiment.
Figure 6I:
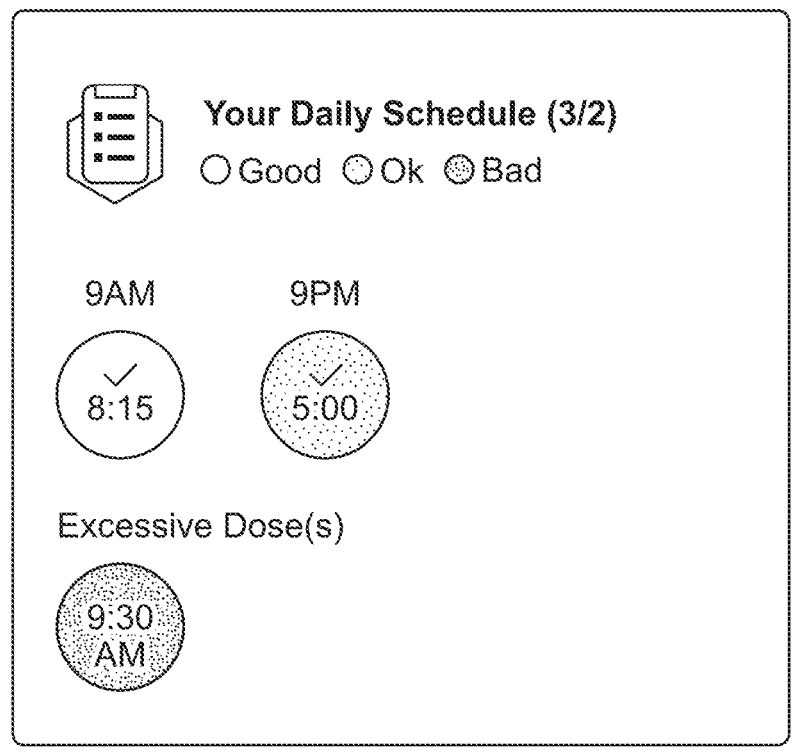

FIGS. 6H and 6I illustrate example display cards 310 that are similar to the example display cards of FIGS. 5H and 5I.

Other types of display cards 310 may also be presented that include information gathered about events related to controller medication doses. For example, the card 310n of FIG. 3H may display the controller medication adherence percentage for a given week. In the instance where data has only begun being collected or after a prolonged gap in data reported to the server 130, from day 2 up until day 7 a partial week's data will be displayed as the current week's adherence percentage, and from day 7 up until day 14 the previous 7 day's adherence percentage (rolling 7 days) will be displayed as the current week's adherence percentage. After day 14 of continuously collected data, the previous 7 day's adherence percentage (rolling 7 days) will be displayed, compared to the adherence percentage of the rolling 7 day period that precedes it.

V.C. Missed Doses and Reminders

Although the examples illustrated with respect to the first and second embodiments above are all related to recommendations about whether to take an upcoming dose, it is contemplated that there will also be scenarios where the patient does not take a scheduled dose, either on time, within the narrow window, within the extended window, or even in between those windows on either side of two adjacent planned dose times. In these instances, the module 131 will generate a notification to be either pushed to the client device 110 or shown next time the software application supporting server 130 is viewed by the patient 111. This notification may include a display card 310 (not explicitly shown) either reminding the patient to take a dose and/or reminding them to take a dose within one of the windows of the next planned dose.

It is further possible that the patient did in fact take the dose, but for device or connectivity issues the taking of the dose was not registered by one of the physical devices configured to report or relay the controller medication event to the server 130. For example, if the medicament device 160 or the sensor 120 had some form of mechanical, electrical, or digital error, or if one of the sensor 120 or client device 110 could not communicate with the server 130, for example due to wireless service (e.g., 802.11) or BLUETOOTH service being interrupted, an event may not be reported.

Although service 130 may receive some information about what kind of error is occurring (e.g., a dedicated hardware hub for sensor 120 is uninstalled, or the supporting software application on client device 110 has been deactivated or uninstalled), regardless of the type of error the server 130 experiences the error as a lack of event data that will affect its ability to provide useful recommendations regarding controller medication dosing.

To address this issue, the server 130 is configured to send notifications to the client device 110 and/or the patient's and/or healthcare providers email and SMS accounts that request status from the patient 111. These notifications encourage them to reactivate or connect any involved computing hardware (e.g., the sensor 120, client device 110) or software (the supporting software application), as well as enter any controller medication events that may have occurred in the intervening period. The notifications may include information about the gap of time that has occurred to provide the patient 111 with a window for which to provide data.

The timing and form of these notifications may vary, both based on type of error (e.g., knowing that BLUETOOTH is off vs. not knowing why no event data has been received), and also based on the amount of time since an event or any other kind of data has been reported from the software application 115, device 110, sensor 120, or medicament device 160. In one embodiment, over a month period more notifications of increasing variety (e.g., display card, email, SMS, personal phone call) are transmitted as the duration since the last reported data increases. For example, separate reminders about the error or lack of data may be sent at days 2, 4, 7, 14, 17, 21, 24, and 28 since last reporting.

In one embodiment, the notification is a card 310 such as the card of FIG. 5L that includes the time of the last synchronization. If the user's last dose time is after the last sensor sync event, the card 310 will show that the sensor 120 and the client 110 need to synchronize before the server 130 can determine if the last dose was on or off schedule.

VI. Additional Considerations

It is to be understood that the figures and descriptions of the present disclosure have been simplified to illustrate elements that are relevant for a clear understanding of the present disclosure, while eliminating, for the purpose of clarity, many other elements found in a typical system. Those of ordinary skill in the art may recognize that other elements and/or steps are desirable and/or required in implementing the present disclosure. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

Some portions of above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope of this description.

What is claimed is:

1. A method comprising:
   receiving a first controller medication usage event recorded at a first recorded time from a computing device associated with a medicament device;
   determining whether the first recorded time is within a first time window inclusive of a first scheduled time for a planned dose specified in a controller medication dosage plan;
   in response to determining that the first recorded time is not within the first time window, characterizing the first event as an off-schedule dose;
   receiving a second controller medication usage event recorded at a second recorded time later than the first recorded time from the computing device;
   determining whether the second recorded time is within the first time window;
   in response to determining that the second recorded time is within the first time window, recharacterizing the first event as an excessive dose and characterizing the second event as an on-time dose;
   in response to characterizing the first event as the off excessive dose, generating a notification indicative of the characterization of the first event as the excessive dose; and
   providing the notification to the computing device.

2. The method of claim 1, wherein the first scheduled time is in the middle of the first time window.

3. The method of claim 1, wherein the notification recommends a patient of the medicament device to skip a subsequent dose.

4. The method of claim 1, event further comprising:
   in response to determining that the first recorded time and the second recorded time are not within the first time window, determining whether the first recorded time or the second recorded time is closer to the first scheduled time;
   in response to determining that the first recorded time is closer to the first scheduled time, characterizing the second event as an excessive dose; and
   in response to determining that the second recorded time is closer to the first scheduled time:
      recharacterizing the first event as an excessive dose, and
      characterizing the second event as an off-schedule dose.

5. The method of claim 1, wherein the controller medication dosage plan further specifies a second scheduled time for another planned dose, the method further comprising:
   in response to determining that the second recorded time is not within the first time window:
      determining whether the second recorded time is within a second time window inclusive of the second scheduled time,
      in response to determining that the second recorded time is within the second time window, characterizing the second event as an on-time dose; and
      in response to determining that the second recorded time is not within the second time window, characterizing the second event as an off-schedule dose.

6. The method of claim 5, further comprising:
   generating a notification indicative of the characterization of the second event.

7. The method of claim 1, further comprising:
   wherein in response to determining that the first recorded time is within the time window, characterizing the first event as an on-time dose;
   in response to determining that the first recorded time and the second recorded time are within the first time window, determining whether the first recorded time or the second recorded time is closer to the first scheduled time;
   in response to determining that the first recorded time is closer to the first scheduled time, characterizing the second event as an excessive dose; and
   in response to determining that the second recorded time is closer to the first scheduled time:
      recharacterizing the first event as an excessive dose, and
      characterizing the second event as an on-time dose.

8. The method of claim 7, further comprising:
in response to characterizing the second event as the excessive dose, generating a second notification based on the characterization; and
providing the second notification to the computing device.

9. A non-transitory computer-readable storage medium storing instructions that, when executed by a processor, cause the process to perform steps comprising:
receiving a first controller medication usage event recorded at a first recorded time from a computing device associated with a medicament device;
determining whether the first recorded time is within a first time window inclusive of a first scheduled time for a planned dose specified in a controller medication dosage plan;
in response to determining that the first recorded time is not within the first time window, characterizing the first event as an off-schedule dose;
receiving a second controller medication usage event recorded at a second recorded time later than the first recorded time from the computing device;
determining whether the second recorded time is within the first time window;
in response to determining that the second recorded time is within the first time window, recharacterizing the first event as an excessive dose and characterizing the second event as an on-time dose;
in response to characterizing the first event as the excessive dose, generating a notification based on the characterization of the first event as the excessive dose; and
providing the notification to the computing device.

10. The storage medium of claim 9, wherein the first scheduled time is in the middle of the first time window.

11. The storage medium of claim 9, wherein the notification recommends a patient of the medicament device to skip a subsequent dose.

12. The storage medium of claim 9, event the steps further comprising:
in response to determining that the first recorded time and the second recorded time are not within the first time window, determining whether the first recorded time or the second recorded time is closer to the first scheduled time;
in response to determining that the first recorded time is closer to the first scheduled time, characterizing the second event as an excessive dose; and
in response to determining that the second recorded time is closer to the first scheduled time:
recharacterizing the first event as an excessive dose, and
characterizing the second event as an off-schedule dose.

13. The storage medium of claim 9, wherein the controller medication dosage plan further specifies a second scheduled time, the steps further comprising:
in response to determining that the second recorded time is not within the first time window:
determining whether the second recorded time is within a second time window inclusive of the second scheduled time,
in response to determining that the second recorded time is within the second time window, characterizing the second event as an on-time dose; and
in response to determining that the second recorded time is not within the second time window, characterizing the second event as an off-schedule dose.

14. The storage medium of claim 13, the steps further comprising:
generating a notification based on the characterization of the second event.

15. The storage medium of claim 9, the steps further comprising:
wherein in response to determining that the first recorded time is within the time window, characterizing the first event as an on-time dose;
in response to determining that the first recorded time and the second recorded time are within the first time window, determining whether the first recorded time or the second recorded time is closer to the first scheduled time;
in response to determining that the first recorded time is closer to the first scheduled time, characterizing the second event as an excessive dose; and
in response to determining that the second recorded time is closer to the first scheduled time:
recharacterizing the first event as an excessive dose, and
characterizing the second event as an on-time dose.

16. The storage medium of claim 15, the steps further comprising:
in response to characterizing the second event as the excessive dose, generating a second notification based on the characterization; and
providing the second notification to the computing device.

* * * * *

UNITED STATES PATENT AND TRADEMARK OFFICE
CERTIFICATE OF CORRECTION

PATENT NO. : 10,643,742 B2
APPLICATION NO. : 16/292303
DATED : May 5, 2020
INVENTOR(S) : Christopher Hogg et al.

Page 1 of 1

It is certified that error appears in the above-identified patent and that said Letters Patent is hereby corrected as shown below:

In the Claims

In Column 23, Claim 12, Line 37, delete "event the" and insert -- the --, therefor.

Signed and Sealed this
Twenty-fourth Day of January, 2023

Katherine Kelly Vidal
*Director of the United States Patent and Trademark Office*